US007605273B2

(12) United States Patent
Dyckman et al.

(10) Patent No.: US 7,605,273 B2
(45) Date of Patent: Oct. 20, 2009

(54) ARYL-SUBSTITUTED PYRAZOLE-AMIDE COMPOUNDS USEFUL AS KINASE INHIBITORS

(75) Inventors: Alaric J. Dyckman, Lawrenceville, NJ (US); Jagabandhu Das, Mercerville, NJ (US); Katerina Leftheris, Skillman, NJ (US); Chunjian Liu, Pennington, NJ (US); Rulin Zhao, Pennington, NJ (US); Bang-Chi Chen, Plainsboro, NJ (US); Stephen T. Wrobleski, Whitehouse Station, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/118,794

(22) Filed: May 12, 2008

(65) Prior Publication Data

US 2008/0275092 A1 Nov. 6, 2008

Related U.S. Application Data

(62) Division of application No. 10/838,129, filed on May 3, 2004, now Pat. No. 7,396,935.

(60) Provisional application No. 60/467,029, filed on May 1, 2003.

(51) Int. Cl.
*C07D 231/14* (2006.01)
(52) U.S. Cl. .................................................. 548/374.1
(58) Field of Classification Search ................ 548/374.1
See application file for complete search history.

(56) References Cited

U.S. PATENT DOCUMENTS

| 5,498,274 | A | 3/1996 | Matsumoto et al. | |
|---|---|---|---|---|
| 5,998,424 | A | 12/1999 | Galemmo, Jr. et al. | |
| 6,020,357 | A | 2/2000 | Pinto et al. | |
| 6,455,520 | B1 | 9/2002 | Brown et al. | |
| 6,686,467 | B2 | 2/2004 | Brown et al. | |
| 6,706,711 | B2 | 3/2004 | Hale | |
| 7,151,113 | B2 | 12/2006 | Dyckman et al. | |
| 7,396,935 | B2 * | 7/2008 | Dyckman et al. | 546/275.4 |
| 2005/0004176 | A1 | 1/2005 | Dyckman et al. | |

FOREIGN PATENT DOCUMENTS

| EP | 1102743 | 5/2001 |
|---|---|---|
| EP | 1102758 | 5/2001 |
| JP | 04316559 | 11/1992 |
| WO | WO 99/58523 | 11/1999 |
| WO | WO00/47558 | 8/2000 |
| WO | WO01/36376 | 5/2001 |
| WO | WO01/46172 | 6/2001 |
| WO | WO01/53274 | 7/2001 |
| WO | WO01/70671 | 9/2001 |
| WO | WO02/36576 | 5/2002 |
| WO | WO02/062804 | 8/2002 |
| WO | WO03/037274 | 5/2003 |
| WO | WO 03037274 | * 5/2003 |
| WO | WO03/064389 | 8/2003 |
| WO | WO 00/75131 | 12/2003 |
| WO | WO2004/014844 | 2/2004 |

OTHER PUBLICATIONS

Jackson et al. (J. Pharm. Exptl. Therap., v. 284, n. 2, 1998, p. 687-692).*
R. N. Atkinson et al., Database CAPLUS on STN, AN:2003-356201, "Pyrazolecarboxamides and sulfonamides as sodium channel blockers", Nov. 1, 2002.
Wang, A.X. et al. Bioorganic & Medicinal Chemistry Letters, Oxford GB, vol. 8, No. 19, pp. 2787-2792 (1998).

* cited by examiner

*Primary Examiner*—Rebecca L Anderson
*Assistant Examiner*—Robert Havlin
(74) *Attorney, Agent, or Firm*—Laurelee A. Duncan

(57) ABSTRACT

The present invention relates to compounds having the formula, and pharmaceutically-acceptable salts, prodrugs, solvates, isomers, and/or hydrates thereof, wherein Q is an optionally-substituted phenyl, pyridyl, pyridazinyl, pyrimidinyl, or pyrazinyl ring; $R_2$ is alkyl or an amino group as defined herein; and Z is optionally-substituted oxadiazolyl or —C(=O)$NR_6$, wherein $R_6$ is lower alkyl or cyclopropyl. The compounds are surprisingly advantageous in preparing pharmaceutical compositions for treating p38 kinase related conditions and/or in methods of treating conditions associated with the activity of p38 kinase in a patient.

14 Claims, No Drawings

ARYL-SUBSTITUTED PYRAZOLE-AMIDE COMPOUNDS USEFUL AS KINASE INHIBITORS

RELATED APPLICATIONS

This application is a Divisional of U.S. patent application Ser. No. 10/838,129, filed May 3, 2004 which claims the benefit of priority under 35 USC §119 of U.S. patent application Ser. No. 60/467,029, filed May 1, 2003. This application is related to U.S. patent application Ser. No. 10/837,778, filed May 3, 2004 and U.S. patent application Ser. No. 10/838,006 filed May 3, 2004, incorporated herein, both of which also are assigned to the present assignee, filed concomintantly herewith, and which claim the benefit of priority of U.S. patent application Ser. No. 60/467,029, filed May 1, 2003.

FIELD OF THE INVENTION

This invention relates to pyrazole-derived compounds useful for treating p38 kinase-associated conditions. The invention further pertains to pharmaceutical compositions containing at least one compound according to the invention useful for treating p38 kinase-associated conditions, and methods of inhibiting the activity of p38 kinase in a mammal.

BACKGROUND OF THE INVENTION

A large number of cytokines participate in the inflammatory response, including IL-1, IL-6, IL-8 and TNF-α. Overproduction of cytokines such as IL-1 and TNF-α are implicated in a wide variety of diseases, including inflammatory bowel disease, rheumatoid arthritis, psoriasis, multiple sclerosis, endotoxin shock, osteoporosis, Alzheimer's disease, and congestive heart failure, among others [Henry et al., *Drugs Fut.*, Vol. 24 (1999), at pp. 1345-54; Salituro et al., *Curr. Med. Chem.*, Vol. 6 (1999), at pp. 807-823]. Evidence in human patients indicates that protein antagonists of cytokines are effective in treating chronic inflammatory diseases, such as, for example, monoclonal antibody to TNF-α (Enbrel) [Rankin et al., *Br. J. Rheumatol.*, Vol. 34 (1995), at pp. 334-42], and soluble TNF-α receptor-Fc fusion protein (Etanercept) [Moreland et al., *Ann. Intern. Med.*, Vol. 130 (1999), at pp. 478-86].

The biosynthesis of TNF-α occurs in many cell types in response to an external stimulus, such as, for example, a mitogen, an infectious organism, or trauma. Important mediators of TNF-α production include the mitogen-activated protein (MAP) kinases, a family of Ser/Thr protein kinases that activate their substrates by phosphorylation. The MAP kinases are activated in response to various stress stimuli, including but not limited to proinflammatory cytokines, endotoxin, ultraviolet light, and osmotic shock.

One important MAP kinase is p38 kinase, also known as cytokine suppressive anti-inflammatory drug binding protein (CSBP) or IK. Activation of p38 requires dual phosphorylation by upstream MAP kinase kinases (MKK3 and MKK6) on threonine and tyrosine within a Thr-Gly-Tyr motif characteristic of p38 isozymes. There are four known isoforms of p38, i.e., p38-α, p38β, p38γ, and p38δ. The α and β isoforms are expressed in inflammatory cells and are key mediators of TNF-α production. Inhibiting the p38α and β enzymes in cells results in reduced levels of TNF-α expression. Also, administering p38α and β inhibitors in animal models of inflammatory disease has established the effectiveness of these inhibitors in treating those diseases. The present invention provides pyrazole-derived compounds, useful as kinase inhibitors, in particular, as inhibitors of p38α and β kinase.

DESCRIPTION OF THE INVENTION

The present invention pertains to compounds having the formula (I),

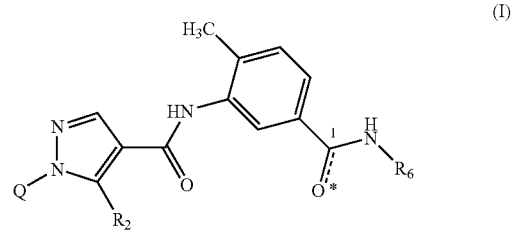

(I)

and pharmaceutically-acceptable salts, prodrugs, solvates, isomers, and/or hydrates thereof, which are advantageous as inhibitors of p38 kinase, wherein, Q is an optionally-substituted phenyl, pyridyl, pyridazinyl, pyrimidinyl, or pyrazinyl ring;

the bond between the oxygen atom O* and the adjacent carbon atom C1 either (i) is a double bond to define a carbonyl group [C(=O)], wherein $R_6$ is $C_{1-6}$alkyl or cyclopropyl; or (ii) is a single bond, wherein when a single bond, said oxygen atom O* is further bonded to the group $R_6$ and taken together with the adjacent nitrogen atom and $R_6$ define an optionally-substituted oxadiazolyl ring, the bond between C1 and the adjacent nitrogen atom being a double bond; and $R_2$ is selected from $C_{1-6}$alkyl, amino, alkylamino, substituted alkylamino, cycloamino, substituted cycloamino, and $C_{1-6}$alkyl substituted with one to two of amino, alkylamino, substituted alkylamino, cycloamino, and/or substituted cycloamino.

Accordingly, one aspect of the invention relates to compounds having the Formula (Ia),

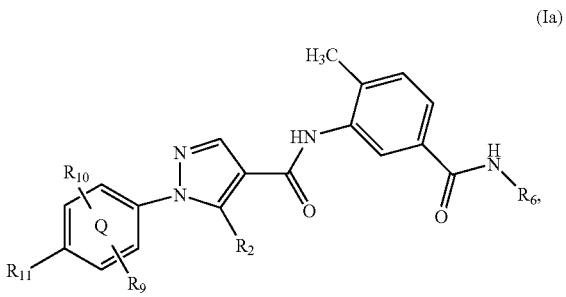

(Ia)

wherein $R_6$ is $C_{1-6}$alkyl or cyclopropyl, $R_2$ is as defined above, Q is phenyl, pyridyl, pyridazinyl, pyrimidinyl, or pyrazinyl, and $R_9$, $R_{10}$, and $R_{11}$ are optional substituents as defined herein for aryl and/or heteroaryl, as well as pharmaceutically-acceptable salts, prodrugs, solvates, isomers, and/or hydrates thereof.

Another aspect of the invention relates to compounds having the formula,

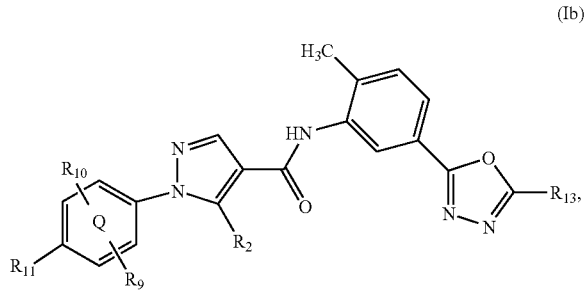

(Ib)

wherein

R$_2$ is as defined above, Q is phenyl, pyridyl, pyridazinyl, pyrimidinyl, or pyrazinyl, and R$_9$, R$_{10}$, R$_{11}$, and R$_{13}$ are optional substituents as defined herein for aryl and/or heteroaryl, as well as pharmaceutically-acceptable salts, prodrugs, solvates, isomers, and/or hydrates thereof.

According to another aspect of the invention, there is provided a method of modulating p38 kinase in a mammal by administering a compound of formula (I), to said mammal. According to another aspect of the invention, there is provided a pharmaceutical composition comprising at least one compound according to formula (I), and/or formulae (Ia) and/or (Ib), and a pharmaceutically-acceptable carrier or diluent. According to another aspect of the invention, there is provided a method of treating an inflammatory disorder comprising administering to a patient a pharmaceutical composition comprising at least one compound according to formula (I), and/or formulae (Ia) and/or (Ib), and a pharmaceutically-acceptable carrier or diluent.

Definitions

The following are definitions of terms used in the present specification and claims. The initial definition provided for a group or term herein applies to that group or term throughout the present specification and claims herein individually or as part of another group, unless otherwise indicated.

The terms "alkyl" and "alk" refer to a straight or branched chain alkane (hydrocarbon) radical containing from 1 to 12 carbon atoms, preferably 1 to 6 carbon atoms. Exemplary "alkyl" groups include methyl, ethyl, propyl, isopropyl, 1-methylpropyl, n-butyl, t-butyl, isobutyl, pentyl, hexyl, isohexyl, heptyl, dimethylpentyl, diethylpentyl, octyl, 2,2,4-trimethylpentyl, nonyl, decyl, undecyl, dodecyl, and the like. The term "$C_1$-$C_4$ alkyl" refers to a straight or branched chain alkane (hydrocarbon) radical containing from 1 to 4 carbon atoms, such as methyl, ethyl, propyl, isopropyl, n-butyl, t-butyl, and isobutyl. A lower alkyl is a "$C_1$-$C_4$ alkyl." When alkyl, lower alkyl (or $C_1$-$C_4$alkyl) is used as a suffix following another named group, such as "hydroxyalkyl" or hydroxyl (lower alkyl), this is intended to refer to an alkyl or lower alkyl ($C_1$-$C_4$alkyl) having bonded thereto one, two or three of the other, specifically-named group(s) at any point of attachment on either the straight or branched chain of the alkyl. As a further example, arylalkyl includes groups such as benzyl or phenylethyl. When the term "substituted" is used with such groups, as in "substituted arylalkyl" or "substituted alkoxyalkyl," it should be understood that either the alkyl moiety, the other named moiety, or both, may be substituted with groups selected from those recited herein as appropriate, e.g., for the alkyl moiety, groups may be selected from those recited below for substituted alkyl, and for the other, specifically-named group, groups may be selected from those recited below for that group.

"Substituted alkyl" refers to an alkyl group as defined above substituted with one or more substituents, preferably 1 to 4 substituents, more preferably 1 to 2 substituents, at any available point of attachment on the straight and/or branched chain. Exemplary substituents may include but are not limited to one or more of halogen, haloalkyl (e.g., a single halo substituent or multiple halo substitutents forming, in the latter case, groups such as a perfluoroalkyl group including for example, —CHCl$_2$ and/or CF$_3$), haloalkoxyl (e.g., including trifluoromethoxy), cyano, nitro, alkenyl, alkynyl, cycloalkyl, heterocycle, heteroaryl, aryl, OR$_a$, SR$_a$, S(=O)R$_e$, S(=O)$_2$R$_e$, P(=O)$_2$R$_e$, S(=O)$_2$OR$_e$, P(=O)$_2$OR$_e$, P(=O)(OR)$_2$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_a$, C(=O)R$_a$, C(=O)NR$_b$R$_c$, OC(=O)R$_a$, C(=O)ONR$_b$R$_c$, OC(=O)NR$_b$R$_c$, NR$_b$C(=O) OR$_a$, NR$_d$C(=O)NR$_b$R$_c$, NR$_d$S(=O)$_2$NR$_b$R$_c$, NR$_d$P(=O)$_2$ NR$_b$R$_c$, NR$_b$C(=O)R$_a$, and/or NR$_b$P(=O)$_2$R$_e$, wherein R$_a$, R$_b$, R$_c$, R$_d$ and R$_e$ are selected from hydrogen, alkyl, alkenyl, aminoalkyl, alkylaminoalkyl, cycloalkyl(alkyl), aryl(alkyl), heterocyclo(alkyl), heteroaryl(alkyl), cycloalkyl, aryl, heterocyclo, and/or heteroaryl, except R$_e$ is not hydrogen; and additionally, when R$_b$ and R$_c$ are attached to the same nitrogen atom, they may be joined together to form a cycloamino group. Each of R$_a$, R$_b$, R$_c$, R$_d$ and/or R$_e$ on the alkyl and/or cyclic moieties in turn may be optionally substituted with one to three groups, preferably substituted with up to two groups (0 to 2 groups), selected from lower alkyl, lower alkenyl, R$_f$, and a lower alkyl or lower alkenyl substituted with one to two R$_f$, wherein R$_f$ is selected from one or more of cyano, halogen, haloC$_1$-C$_4$alkyl, haloC$_1$-C$_4$alkoxy, keto (=O) (where valence allows), nitro, OH, O(C$_1$-C$_4$alkyl), SH, S(C$_1$-C$_4$alkyl), S(=O)(C$_1$-C$_4$alkyl), S(=O)$_2$(C$_1$-C$_4$alkyl), NH$_2$, NH(C$_1$-C$_4$alkyl), N(C$_1$-C$_4$alkyl)$_2$, NH(cycloalkyl), NH(phenyl), phenyl, benzyl, phenoxy, benzyloxy, NHS(=O)$_2$ (alkyl), S(=O)$_2$NH$_2$, S(=O)$_2$NH(C$_1$-C$_4$alkyl), S(=O)$_2$N (C$_1$-C$_4$alkyl)$_2$, S(=O)$_2$NH(cycloalkyl), S(=O)$_2$NH (phenyl), C(=O)OH, C(=O)O(C$_1$-C$_4$alkyl), C(=O)H, C(=O)(C$_1$-C$_4$alkyl), C(=O)NH$_2$, C(=O)NH(C$_1$-C$_4$alkyl), C(=O)N(C$_1$-C$_4$alkyl)$_2$, C(=O)NH(cycloalkyl), C(=O)NH (phenyl), C(=O)ONH$_2$, C(=O)ONH(C$_1$-C$_4$alkyl), C(=O) ON(C$_1$-C$_4$alkyl)$_2$, C(=O)ONH(cycloalkyl), C(=O)ONH (phenyl), NHC(=O)OC$_1$-C$_4$alkyl, N(C$_1$-C$_4$alkyl)C(=O)O (C$_1$-C$_4$alkyl), NHC(=O)NH$_2$, NHC(=O)NH(C$_1$-C$_4$alkyl), NHC(=O)N(C$_1$-C$_4$alkyl)$_2$, NHC(=O)NH(cycloalkyl), NHC(=O)NH(phenyl), NHC(=O)H, and/or NHC(=O) (C$_1$-C$_4$alkyl).

The term "alkenyl" refers to a straight or branched chain hydrocarbon radical containing from 2 to 12 carbon atoms and at least one carbon-carbon double bond. Exemplary such groups include ethenyl and allyl. Lower alkenyl means an alkenyl group of 2 to 4 carbon atoms. "Substituted alkenyl" refers to an alkenyl group substituted with one or more substituents, preferably 1 to 4 substituents, more preferably 1 to 2 substituents, at any available point of attachment. Exemplary substituents may include, but are not limited to, alkyl, substituted alkyl, and those groups recited above as exemplary substituents for substituted alkyl groups.

The term "alkynyl" refers to a straight or branched chain hydrocarbon radical containing from 2 to 12 carbon atoms and at least one carbon-to-carbon triple bond. Exemplary such groups include ethynyl. "Substituted alkynyl" refers to an alkynyl group substituted with one or more substituents, preferably 1 to 4 substituents, more preferably 1 to 2 substituents, at any available point of attachment. Exemplary substituents include, but are not limited to, alkyl, substituted alkyl, and those groups recited above as exemplary substituents for substituted alkyl groups.

The term "alkoxy" refers to the group $OR_g$, wherein $R_g$ is selected from alkyl, alkenyl, or cycloalkyl. A $C_1$-$C_4$alkoxy is an alkoxy group $OR_{g'}$ wherein $R_{g'}$ is a $C_1$-$C_4$alkyl or $C_3$-$C_4$cycloalkyl. A substituted alkoxy group is an alkoxy group as defined above wherein at least one of the alkyl, alkenyl, and/or cycloalkyl moieties is substituted with one or more, preferably 1 to 4, more preferably 1 to 2, groups selected from those recited above for substituted alkenyl groups.

The term "amino" refers to $NH_2$, and an alkylamino refers to an amino group wherein one or both of the hydrogen atoms is or are replaced with a group chosen from alkyl, alkenyl, and/or cycloalkyl. Thus, alkylamino refers to the group $NR_hR_i$, wherein $R_h$ and $R_i$ are selected from hydrogen, alkyl, alkenyl, and/or cycloalkyl, provided $R_h$ and $R_i$ are not both hydrogen. "Aminoalkyl" refers to an alkyl group as defined above substituted with an amino group, and an "alkylaminoalkyl" refers to an alkyl group as defined above substituted with one or more alkylamino groups. A substituted alkylamino group is an alkylamino group wherein at least one of the alkyl, alkenyl, and/or cycloalkyl moieties is substituted with one or more, preferably 1 to 4, more preferably 1 to 2, groups selected from those recited herein as appropriate for the recited moeity. Thus, for example, an optionally-substituted alkylamino group refers to the group —NR'R", wherein R' and R" are selected from hydrogen, alkyl, substituted alkyl, alkenyl, substituted alkenyl, cycloalkyl, and substituted cycloalkyl, provided R' and R" are not both hydrogen, as in that case the group is amino and not optionally-substituted alkylamino.

A cycloamino group refers to a group —NR'R", wherein R' and R" join to form a monocyclic heterocyclo ring, such as, for example, N-morpholinyl, N-piperidinyl, N-piperazinyl and the like. A "substituted cycloamino" is a cycloamino group having one or more, preferably one to 4, more preferably one to 2, substituents selected from those recited below for substituted heterocyclo groups.

The term "alkylthio" refers to the group $SR_g$, wherein $R_g$ is selected from alkyl, alkenyl, and cycloalkyl. A $C_1$-$C_4$alkylthio is an alkylthio group $SR_{g'}$ wherein $R_{g'}$ is a $C_1$-$C_4$alkyl or $C_3$-$C_4$cycloalkyl. A substituted alkylthio group is an alkylthio group wherein at least one of the alkyl, alkenyl, and/or cycloalkyl moieties is substituted with one or more, preferably 1 to 4, more preferably 1 to 2, groups selected from those recited above for substituted alkenyl groups.

The term "aryl" refers to cyclic, aromatic hydrocarbon groups which have 1 to 3 aromatic rings, including phenyl and naphthyl. The aryl group may have fused thereto a second or third ring which is a heterocyclo, cycloalkyl, or heteroaryl ring, provided in that case the point of attachment will be to the aryl portion of the ring system. Thus, exemplary aryl groups include,

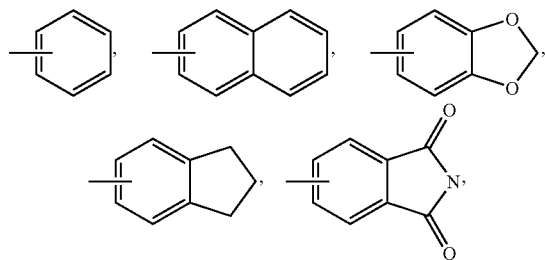

-continued

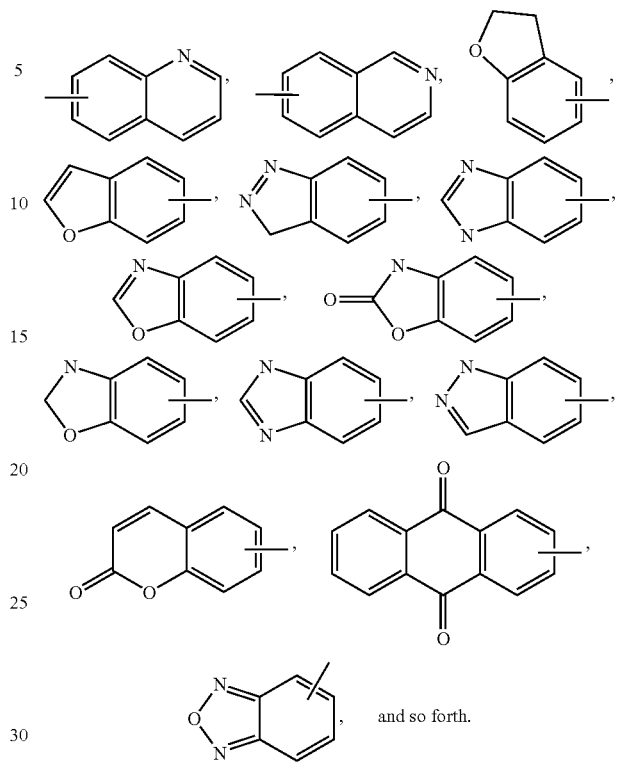

and so forth.

"Substituted aryl" refers to an aryl group substituted by one or more substituents, preferably 1 to 3 substituents, more preferably 1 to 2 substituents, at any point of attachment of the aryl ring and/or of any further ring fused thereto. Exemplary substituents include, but are not limited to, alkyl, substituted alkyl, and where valence allows those groups recited above as exemplary substituents for substituted alkyl groups.

The term "cycloalkyl" refers to a fully saturated and partially unsaturated cyclic hydrocarbon group containing from 1 to 3 rings and 3 to 8 carbons per ring. Exemplary such groups include cyclopropyl, cyclobutyl, cyclopentyl, cyclohexyl, cycloheptyl, cyclobutenyl, cyclopentenyl, cyclohexenyl, etc. A cycloalkyl ring may have a carbon ring atom replaced with a carbonyl group (C=O), as illustrated below. Cycloalkyl groups include such rings having a second or third ring fused thereto that is a heterocyclo, heteroaryl, or aryl group, provided that in such cases the point of attachment is to the cycloalkyl portion of the ring system. The term "cycloalkyl" also includes such rings having a second or third ring attached to the ring or ring system in a spiro fashion wherein the spiro ring is either a heterocyclo or carbocyclic ring. "Substituted cycloalkyl" refers to a cycloalkyl group as defined above having one or more substituents, preferably 1 to 4 substituents, more preferably 1 to 2 substituents, at any available point of attachment on either the cycloalkyl ring and where valence allows on any rings fused or attached thereto. Exemplary substituents include, but are not limited to, alkyl, substituted alkyl, and those groups recited above as exemplary substituents for substituted alkyl groups.

Thus, as an illustration non-limiting examples of cycloalkyl rings may include,

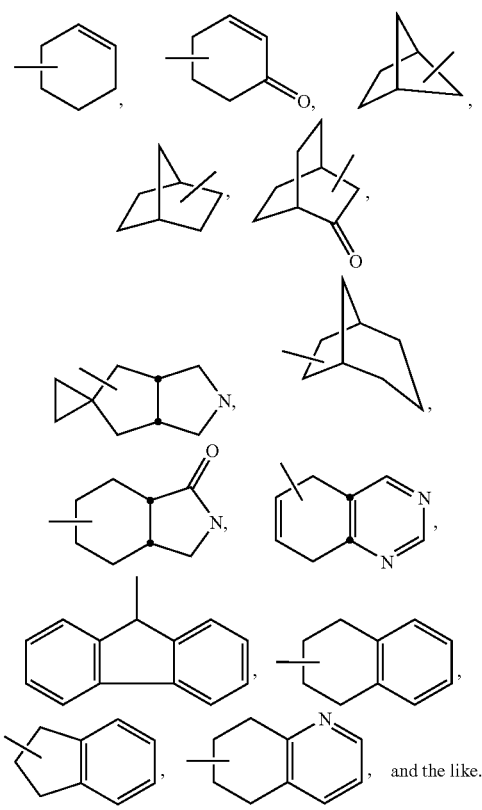

, and the like.

The terms "heterocycle," "heterocyclic" and "heterocyclo" refer to fully saturated or partially unsaturated non-aromatic cyclic groups (for example, 4 to 7 membered monocyclic, 7 to 11 membered bicyclic, or 10 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and/or sulfur heteroatoms may optionally be oxidized and the nitrogen heteroatoms may optionally be quaternized. A heterocyclo ring may have a carbon ring atom replaced with a carbonyl group (C=O), as illustrated above for cycloalkyl groups. The heterocyclic group may be attached to the remainder of the molecule at any nitrogen atom or carbon atom of the ring or ring system. Additionally, the heterocyclo group may have a second or third ring attached thereto in a spiro or fused fashion, provided the point of attachment is to the heterocyclo group. An attached spiro ring may be a carbocyclic or heterocyclic ring and the second and/or third fused ring may be a cycloalkyl, aryl or heteroaryl ring. Exemplary monocyclic heterocyclic groups include azetidinyl, pyrrolidinyl, pyrazolinyl, imidazolidinyl, oxazolidinyl, piperidinyl, piperazinyl, morpholinyl, tetrahyrdofuryl, tetrahydropyranyl, thiamorpholinyl, and the like.

Exemplary bicyclic heterocyclic groups include indolinyl, isoindolinyl, quinuclidinyl, benzopyrrolidinyl, benzopyrazolinyl, benzoimidazolidinyl, benzopiperidinyl, benzopiperazinyl, tetrahydroisoquinolinyl, tetrahydroquinolinyl, dihydroisoindolyl and the like.

"Substituted heterocycle," "substituted heterocyclic," and "substituted heterocyclo" refer to heterocycle, heterocyclic or heterocyclo groups substituted with one or more substituents, preferably 1 to 4 substituents, more preferably 1 to 2 substituents, at any available point of attachment to the heterocyclo ring and/or any ring fused or attached thereto in a spiro fashion. Exemplary substituents include, but are not limited to, alkyl, substituted alkyl, and those groups recited above as exemplary substituents for substituted alkyl groups.

The term "heteroaryl" refers to aromatic cyclic groups (for example, 5 to 6 membered monocyclic, 7 to 11 membered bicyclic, or 10 to 16 membered tricyclic ring systems) which have at least one heteroatom in at least one carbon atom-containing ring. Each ring of the heteroaryl group containing a heteroatom may have 1, 2, 3, or 4 heteroatoms selected from nitrogen atoms, oxygen atoms and/or sulfur atoms, where the nitrogen and/or sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heteroaryl group may be attached to the remainder of the molecule at any nitrogen atom or carbon atom of the ring or ring system. Additionally, the heteroaryl group may have a second or third carbocyclic (cycloalkyl or aryl) or heterocyclic ring fused thereto provided the point of attachment is to the heteroaryl group.

Exemplary monocyclic heteroaryl groups include pyrazolyl, imidazolyl, triazolyl, oxazolyl, furyl, thiazolyl, isoxazolyl, thiazolyl, pyridyl

[i.e., ], pyridazinyl

[i.e., ], pyrimidinyl

[i.e., ], pyrazinyl

[i.e., ], triazinyl, and the like. Unless reference is made to a specific point of attachment, e.g., as in pyrid-2-yl, pyridazin-3-yl, it is intended that such heteroaryl groups can be bonded to another moiety at any available point of attachment.

Exemplary bicyclic heteroaryl groups include benzothiazolyl, benzoxazolyl, benzoxadiazolyl, benzothienyl, quinolinyl, chromenyl, indolyl, indazolyl, isoquinolinyl, benzimidazolyl, benzopyranyl, benzofuryl, benzofurazanyl, benzopyranyl, cinnolinyl, quinoxalinyl, pyrrolopyridyl, furopyridinyl (such as furo[2,3-c]pyridinyl, furo[3,2-b]pyridinyl] or furo[2,3-b]pyridinyl), triazinylazepinyl, and the like.

"Substituted heteroaryl" refers to heteroaryl groups substituted with one or more substituents as valence allows, preferably 1 to 3 substituents, more preferably 1 to 2 substituents, at any available point of attachment to the heteroaryl ring and/or any ring fused thereto. Exemplary substituents include, but are not limited to, alkyl, substituted alkyl, and those groups recited above as exemplary substituents for substituted alkyl groups.

When reference is made to an optionally-substituted, specifically-named aryl, heteroaryl, cycloalkyl, or heterocyclo ring, the optional substituents may be selected as valence allows from the groups recited above for the genus of rings of which the specifically-named group is a member. For example, "optionally-substituted phenyl" includes unsubstituted phenyl rings as well as phenyl rings containing one or more substituents selected from those recited above for aryl groups. "Optionally-substituted pyridyl, pyridazinyl, pyrimidinyl, and pyrazinyl," includes unsubstituted pyridyl, pyridazinyl, pyrimidinyl, and pyrazinyl rings, as well as such rings containing one or more substituents selected from those recited above for heteroaryl groups.

The term "optionally substituted oxadiazolyl" as used herein is intended to refer to the group,

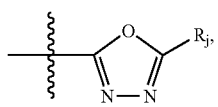

wherein $R_j$ is selected from a substituent recited above for substituted heteroaryl groups.

The term "quaternary nitrogen" refers to a tetravalent positively charged nitrogen atom including, for example, the positively charged nitrogen in a tetraalkylammonium group (e.g., tetramethylammonium, N-methylpyridinium), the positively charged nitrogen in protonated ammonium species (e.g., trimethyl-hydroammonium, N-hydropyridinium), the positively charged nitrogen in amine N-oxides (e.g., N-methylmorpholine-N-oxide, pyridine-N-oxide), and the positively charged nitrogen in an N-amino-ammonium group (e.g., N-aminopyridinium).

The terms "halogen" or "halo" refer to chlorine, bromine, fluorine and/or iodine.

The term haloalkyl refers to an alkyl group having a single halo substituent or multiple halo substitutents forming, for example, groups such as a perfluoroalkyl group including trichloromethyl or trifluoromethyl ($CCl_3$ or $CF_3$). A halo$C_1$-$C_4$alkyl refers to a $C_1$-$C_4$alkyl having one or more halo substituents.

The term haloalkoxy refers to an alkoxy group as defined above wherein the alkyl moiety has a single halo substituent or multiple halo substitutents forming, for example, groups such as a trifluoromethoxy. A halo$C_1$-$C_4$alkoxy refers to a $C_1$-$C_4$alkoxy having one or more halo substituents.

The term "saturated" when used herein is intended to refer to fully saturated and partially saturated moieties, and conversely, "unsaturated" refers to fully unsaturated and partially unsaturated moieties.

When a functional group is termed "protected", this means that the group is in modified form to mitigate, especially preclude, undesired side reactions at the protected site. Suitable protecting groups for the methods and compounds described herein include, without limitation, those described in standard textbooks, such as Greene, T. W. et al., *Protective Groups in Organic Synthesis*, Wiley, N.Y. (1999).

The term "selective" as used herein with reference to the capability of the claimed compounds to inhibit p38 activity means that the compound in question has a level of activity as measured in enzyme assays for inhibiting the p38 α/β kinase that is significantly greater than the activity of the compound in inhibiting a plurality of other kinases falling within families throughout the human kinome. The term "significantly greater activity" includes the activity of at least one compound having about 500-fold or more greater activity for inhibiting p38α/β enzyme as compared with the activity of the compound in inhibiting other kinases, for example, as compared with the activity of the compound in inhibiting about twenty-five or more other kinases, in another example, as compared with about fifty or more other kinases, and in yet another example, as compared with about 100 or more other kinases. Thus, a selective p38 inhibitor as defined herein according to one embodiment will inhibit the α-isoform of the p38 kinase, the β-isoform of the p38 kinase, and/or both the α and β forms of the p38 kinase, at least 500 times greater than it will inhibit any one of a plurality of other kinases. Thus, for example, considering an embodiment involving comparison with a sample of twenty-five other kinases, p38 selective compounds will have 500 times greater activity in inhibiting p38α/β kinase as compared with any one of each of the twenty-five other kinases considered individually (e.g., in a one-on-one comparison). In another embodiment of the invention, compounds are provided having at least about 1,000-fold greater activity for inhibiting p38 α/β kinase as compared with other kinases, for example, as compared with about twenty-five or more, about fifty or more, and in yet another example, as compared with about 100 or more other kinases. In yet another embodiment of the invention, compounds are provided having at least about 5,000-fold greater activity for inhibiting p38 α/β kinase as compared with other kinases, for example, as compared with about twenty-five or more other kinases, as compared with about fifty or more other kinases, and in yet another example, as compared with about 100 or more other kinases. The term "highly selective" as used herein means the compound in question has at least about 10,000 fold greater activity for inhibiting the p38 α/β kinase enzyme as compared with at least thirty other kinases, more preferably, as compared with at least about fifty or more other kinases. When reference is made herein to "other kinases", applicant intends to refer to kinases known in the field other than the p38 α/β kinases. For example, various known kinases and kinase families other than the 38 α/β kinase are identified in WO 02/062804, and in Manning, G. et al., *The Protein Kinase Complement of theHuman Genome, Science* (Washington, D.C., United States) (2002), 298(5600), at pp. 1912-1916, 1933-1934, which is incorporated herein by reference. "Other kinases" as identified therein thus may include, without limitation, one or more kinases chosen from the following kinases and/or kinase families: CaMK1, CaMK2, CDK, DAPK, EMT, FGF, FMS, GSK3, LCK, PDGF-R, PKA, PCK, RAF, RIPK, LIMK-1, SYK, Met, PAK-4, PAK-5, ZC-1, STLK-2, DDR-2, Aurora 1, Aurora 2, Bub-1, PLK, Chk1, Chk2, HER2, JAK, raf1, MEK1, EGF-R, RSK/RSK, IGF-R, IRAK, VEGF-R, PI3K, PDK, HIPK, STKR, BRD, Wnk, NKF3, NKF4, NKF5, weel kinase, Src, Ab1, ILK, MK-2, IKK-2, RIPK, Cdc7, Ste11, Ste20, Ste7, Tec, Trk, and/or Nek, and so forth. The above is an exemplary, non-limiting list of other kinases. Manning identified 518 protein kinases, and applicant intends to incorporate each one of these 518 protein kinases other than the p38 kinase in the definition of the term "other kinases" as used herein.

There are many enzyme assays known in the field that may be used to measure the levels of activity to determine selectivity. Applicant has described certain enzyme assays below but does not intend to be limited to use of these specific assays with regard to the definition of selectivity herein.

Unless otherwise indicated, a heteroatom with an unsatisfied valence is understood to have hydrogen atoms sufficient to satisfy the valences, as one skilled in the field will appreciate.

The compounds of formula I may form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts may also be useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety, such as but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug" as employed herein denotes a compound which, upon administration to a subject, undergoes chemical conversion by metabolic or chemical processes to yield a compound of the formula I, or a salt and/or solvate thereof. Solvates of the compounds of formula I include, for example, hydrates.

Compounds of the formula I, and salts thereof, may exist in their tautomeric form (for example, as an amide or imino ether). All such tautomeric forms are contemplated herein as part of the present invention.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclo rings.

When reference is made herein to a compound of formula (I) herein, this is intended to refer to each compound of formula (I), and each salt, prodrug, solvate, or isomer thereof, alone or in combination with other compounds of formula (I), other salts, prodrugs, solvates, or isomers of compounds of formula (I), or other compounds not of formula (I), without limitation to the manner in which said compound of formula (I), or salt, prodrug, solvate, or isomer thereof is made or formed, for example, whether existing in a pure form, isolated form, crude form, together with one or more excipients or impurities, existing in a solid or liquid form, in a pharmaceutical preparation before administration to a patient, as formed in the body of a patient after administration to a patient, and so forth.

Throughout the specification, groups and substituents thereof may be chosen to provide stable moieties and compounds.

Alternate Embodiments

Alternate genuses and/or subgenuses of the compounds of the present invention include compounds of the formulae (Ia), (Ib) and/or (Ic), and/or pharmaceutically acceptable salts, hydrates, isomers, prodrugs, and/or solvates thereof. According to one aspect of the invention, there are provided compounds having the formula (Ia):

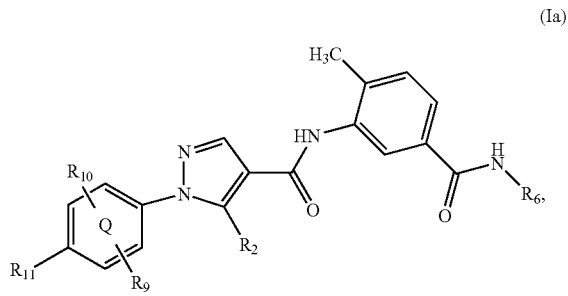
(Ia)

wherein,

R$_6$ is C$_{1-6}$alkyl or cyclopropyl;

R$_2$ is selected from C$_{1-6}$alkyl, NR$_7$R$_8$, and C$_{1-4}$alkyl substituted with a group NR$_7$R$_8$;

R$_7$ and R$_8$ are independently selected from hydrogen, C$_{1-6}$alkyl, and C$_{3-6}$cycloalkyl, wherein each of said groups R$_7$ and R$_8$ are in turn optionally substituted with one to two of OH, O(C$_{1-4}$alkyl), heteroaryl, heterocylo, NH$_2$, NH(C$_{1-4}$alkyl), and/or N(C$_{1-4}$alkyl)$_2$, or alternatively, R$_7$ and R$_8$ are taken together with the nitrogen atom to which they are attached to form a cycloamino group;

Q is phenyl, pyridyl, pyridazinyl, pyrimidinyl, or pyrazinyl, and R$_9$, R$_{10}$, and R$_{11}$ are optional substituents as defined herein for aryl and/or heteroaryl groups, as well as pharmaceutically-acceptable salts, prodrugs, solvates, isomers, and/or hydrates thereof.

According to another aspect of the invention, there are provided compounds as immediately defined above wherein R$_7$ and R$_8$ are independently selected from hydrogen, C$_{1-6}$alkyl, and C$_{3-6}$cycloalkyl, wherein each of said groups R$_7$ and R$_8$ are in turn optionally substituted with one to two of OH, O(C$_{1-4}$alkyl), imidazolyl, pyridyl, tetrahydrofuryl, NH$_2$, NH(C$_{1-4}$alkyl), N(C$_{1-4}$alkyl)$_2$, and N-morpholinyl, or alternatively, R$_7$ and R$_8$ are taken together with the nitrogen atom to which they are attached to form a morpholinyl, piperidinyl, or piperazinyl ring; and Q is phenyl or pyridyl, and R$_9$, R$_{10}$, and R$_{11}$ are optional substituents as defined herein for aryl and/or heteroaryl groups, as well as pharmaceutically-acceptable salts, prodrugs, solvates, isomers, and/or hydrates thereof.

In another embodiment, compounds are provided as immediately defined above wherein R$_9$, R$_{10}$, and R$_{11}$ are selected from hydrogen, C$_{1-4}$alkyl, O(C$_{1-4}$alkyl), halogen, haloC$_{1-4}$alkyl, cyano, SO$_2$(C$_{1-4}$alkyl), and/or nitro.

In yet another embodiment, compounds are provided as immediately defined above, wherein R$_2$ is methyl, ethyl, propyl, butyl, or NR$_7$R$_8$, wherein R$_7$ is hydrogen or C$_{1-4}$alkyl, and R$_8$ is hydrogen, C$_{1-4}$alkyl, C$_{3-6}$cycloalkyl, or a C$_{1-4}$alkyl substituted with OH, methoxy, pyridyl, tetrahydrofuryl, NH$_2$, NHC$_{1-4}$alkyl, N(C$_{1-4}$alkyl)$_2$, imidazolyl, and N-morpholinyl; or alternatively, R$_7$ and R$_8$ combine to form morpholinyl, piperidinyl, or piperazinyl.

According to another embodiment of the invention, there are provided compounds having the formula (I) and/or (Ia) above, wherein ring Q is a group

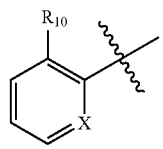

wherein R$_{10}$ is halogen, cyano, or trifluoromethyl, and X is CH or N, and/or a pharmaceutically-acceptable salt, prodrug, solvate, isomer, and/or hydrate thereof.

In yet another embodiment, there are provided compounds having the formula

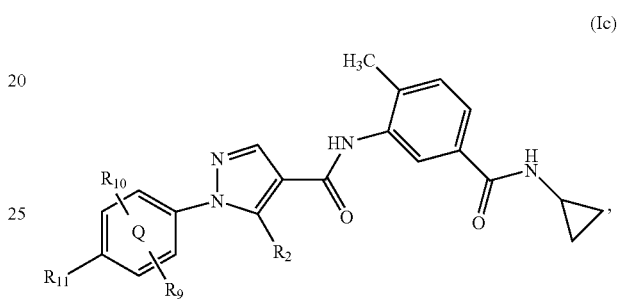
(Ic)

wherein R$_2$ is as defined above, Q is phenyl, pyridyl, pyridazinyl, pyrimidinyl, or pyrazinyl, and R$_9$, R$_{10}$, and R$_{11}$ are optional substituents as defined herein for aryl and/or heteroaryl, as well as pharmaceutically-acceptable salts, prodrugs, solvates, isomers, and/or hydrates thereof.

In yet another embodiment, compounds are provided having the formulae (Ia) and/or (Ic), above, wherein R$_9$, R$_{10}$, and R$_{11}$ are selected from hydrogen, C$_{1-4}$alkyl, O(C$_{1-4}$alkyl), halogen, haloC$_{1-4}$alkyl, cyano, SO$_2$(C$_{1-4}$alkyl), and/or nitro; R$_2$ is selected from C$_{1-4}$alkyl, N-morpholinyl, NH$_2$, and/or NR$_7$R$_8$, wherein R$_7$ is hydrogen or C$_{1-4}$alkyl and R$_8$ is C$_{1-4}$alkyl, C$_{3-6}$cycloalkyl, or a C$_{1-4}$alkyl substituted with OH, methoxy, pyridyl, tetrahydrofuryl, N(CH$_3$)$_2$, imidazolyl, and/or N-morpholinyl.

Another aspect of the invention relates to compounds having the formula,

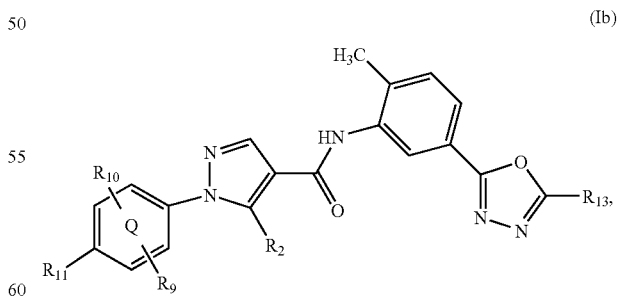
(Ib)

wherein R$_2$ is as defined above, Q is phenyl, pyridyl, pyridazinyl, pyrimidinyl, or pyrazinyl, and R$_9$, R$_{10}$, R$_{11}$, and R$_{13}$ are optional substituents as defined herein for aryl and/or heteroaryl groups, as well as pharmaceutically-acceptable salts, prodrugs, solvates, isomers, and/or hydrates thereof.

In another embodiment, there are provided compounds as immediately defined above wherein $R_{13}$ is lower alkyl or phenyl, more preferably, wherein $R_{13}$ is methyl.

In another embodiment, compounds are provided having the formula (Ib), above, wherein $R_9$, $R_{10}$, and $R_{11}$ are selected from hydrogen, $C_{1-4}$alkyl, $O(C_{1-4}$alkyl), halogen, halo$C_{1-4}$alkyl, cyano, $SO_2(C_{1-4}$alkyl), and/or nitro; $R_2$ is selected from $C_{1-4}$alkyl, N-morpholinyl, $NH_2$, and/or $NR_7R_8$, wherein $R_7$ is hydrogen or $C_{1-4}$alkyl and $R_8$ is $C_{1-4}$alkyl, $C_{3-6}$cycloalkyl, or a $C_{1-4}$alkyl substituted with OH, methoxy, pyridyl, tetrahydrofuryl, $N(CH_3)_2$, imidazolyl, and/or N-morpholinyl.

In another embodiment, there are provided compounds having the formula,

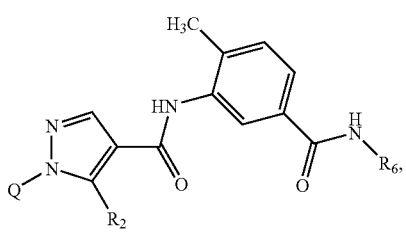

wherein $R_2$ and $R_6$ are as defined above for compounds of formula (Ia), and Q may be selected from,

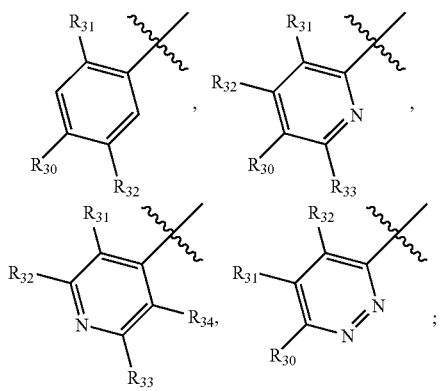

wherein $R_{30}$, $R_{31}$, $R_{32}$, $R_{33}$ and $R_{34}$ are selected from hydrogen, halogen, cyano, trifluoromethyl, trifluoromethoxy, $C_{1-4}$alkyl, $O(C_{1-4}$alkyl), nitro, and/or $SO_2CH_3$.

In yet another embodiment, there are provided compounds having the formula,

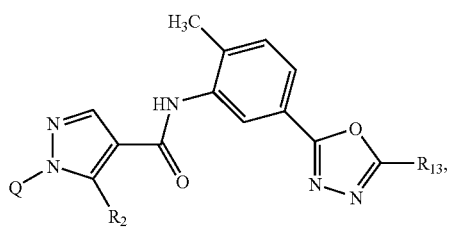

wherein $R_2$ and $R_{13}$ are as defined above for compounds of formula (Ib), and Q may be selected from,

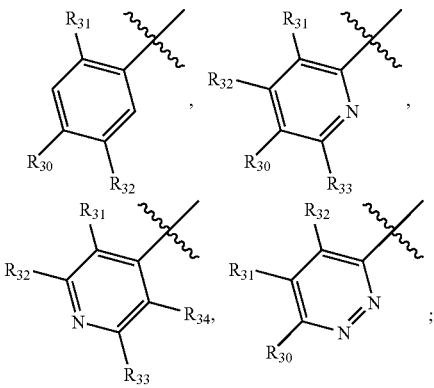

wherein $R_{30}$, $R_{31}$, $R_{32}$, $R_{33}$ and $R_{34}$ are selected from hydrogen, halogen, cyano, trifluoromethyl, trifluoromethoxy, $C_{1-4}$alkyl, $O(C_{1-4}$alkyl), nitro, and/or $SO_2CH_3$.

In compounds of formula (Ia), (Ib), and/or (Ic), another embodiment involves compounds wherein $R_2$ is lower alkyl or amino, more preferably methyl or amino.

Further embodiments will be apparent to one skilled in the field upon considering the disclosure herein, including without limitation the various compounds and moieties thereof set forth in the schemes and examples below.

Utility

The compounds of the invention are inhibitors of p38 kinase, and in particular, isoforms p38α and p38β. Accordingly, compounds of formula (I) have utility in treating conditions associated with p38 kinase activity. Such conditions include diseases or disorders in which cytokine levels are modulated as a consequence of intracellular signaling via p38, and in particular, diseases that are associated with an overproduction of cytokines IL-1, IL-4, IL-8, and TNF-α. As used herein, the terms "treating" or "treatment" encompass responsive and/or prophylaxis measures addressed to the disease state and/or its sypmtoms, e.g., measures designed to inhibit or delay the onset of the disease or disorder, achieve a full or partial reduction of the symptoms or disease state, and/or alleviate, lessen, or cure the disease and/or its symptoms. When reference is made herein to inhibition of "p-38α/β kinase," this means that either or both p38α and p38β kinase are inhibited.

In view of their activity as inhibitors of p-38α/β kinase, compounds of Formula (I) are useful in treating inflammatory diseases, autoimmune diseases, destructive bone disorders, proliferative disorders, angiogenic disorders, infectious diseases, neurodegenerative diseases, viral diseases, and ischemia reperfusion conditions.

More particularly, the inventive compounds may be used to treat inflammatory diseases including, but not limited to, arthritis (e.g., rheumatoid arthritis, lyme disease arthritis, osteoarthritis, traumatic arthritis, rubella arthritis, psoriatic arthritis, gouty arthritis, and other arthritic conditions); glomerulonephritis, pancreatitis (acute or chronic), diabetes, diabetic retinopathy, macular degeneration, conjunctivitis, aplastic anemia, thrombocytopenia, gastritis, chronic thyroiditis, chronic active hepatitis, multiple sclerosis, inflammatory bowel disease, ulcerative colitis, Crohn's disease, cachexia (including cachexia secondary to infection, cancer, or heart disease), periodontal disease, Alzheimer's disease, Parkinson's disease, keloid formation, pulmonary sarcoidosis, myasthenia gravis, inflammatory reaction induced by endotoxin, Reiter's syndrome, gout, acute synovitis, diseases characterized by massive neutrophil infiltration, ankylosing spondylitis, influenze, cerebral malaria, silicosis, bone resorption disease, fever, myalgias due to infection, osteoporosis, multiple myeloma-related bone disorder, neurodegenerative disease caused by traumatic injury, and traumatic brain injury.

The inventive compounds may also be used to treat acute or chronic graft vs host reactions (e.g., pancreatic islet allograft), acute or chronic transplant rejection (e.g., kidney, liver, heart, lung, pancreas, bone marrow, cornea, small bowel, skin allografts, skin homografts, heterografts, and/or cells derived from such organs), and skin conditions including, but not limited to scar tissue formation, eczema, atopic dermatitis, contact dermatitis, urticaria, schleroderma, scleraclerma, and psoriasis. The inventive compounds also may be used to treat allergies and respiratory conditions, including asthma, acute respiratory distress syndrome, hayfever, allergic rhinitis, and any chronic pulmonary inflammatory disease such as chronic obstructive pulmonary disease. The compounds further may be used to treat steroid resistance in asthma and allergies.

Additionally, the inventive compounds may be used to treat inflammation associated with autoimmune diseases including, but not limited to, systemic lupus erythematosis, Addison's disease, autoimmune polyglandular disease (also known as autoimmune polyglandular syndrome), and Grave's disease. The inventive compounds may be used to infectious diseases such as sepsis, septic shock, Shigellosis, and *Heliobacter Pylori.*

The compounds may be used to treat viral diseases including herpes simplex type 1 (HSV-1), herpes simplex type 2 (HSV-2), cytomegalovirus, Epstein-Barr, human immunodeficiency virus (HIV), acute hepatitis infection (including hepatitis A, hepatits B, and hepatitis C), HIV infection and CMV retinitis, AIDS, ARC or malignancy, and herpes.

The inventive compounds also may be used to treat angiogenic disorders including solid tumors, ocular neovascularization, and infantile haemangiomas.

In addition, p38 inhibitors of this invention inhibit the expression of inducible pro-inflammatory proteins such as prostaglandin endoperoxide synthase-2 (PGHS-2), also referred to as cyclooxygenase-2 (COX-2). Accordingly, additional conditions that may be treated with the inventive compounds include edema, analgesia and pain, such as neuromuscular pain, headache, pain caused by cancer or surgery, dental pain and arthritis pain. In view of their COX-2 inhibitory activity, the inventive compounds also may be used to treat cancer including without limitation epithelial cancer and adenocarcinoma.

Additionally, the compounds of this invention are useful to treat ischemia, including ischemia resulting from vascular occlusion, cerebral infarction, stroke, and related cerebral vascular diseases (including cerebrovascular accident and transient ischemic attack). Accordingly, the compounds may be used to treat myocardial infarction, coronary artery disease, non-Q wave MI, congestive heart failure, ventricular hypertrophy, cardiac arrhythmias, unstable angina, chronic stable angina, Prinzmetal's angina, high blood pressure, intermittent claudication, silent ischemia, cardiac hypertrophy, and peripheral occlusive arterial disease (e.g., peripheral arterial disease, critical leg ischemia, prevention of amputation, and prevention of cardiovascular morbidity such as MI, stroke or death).

Additionally, in view of their activity in treating ischemia, the compounds of the invention may be useful to treat symptoms or consequences occurring from thrombosis, atherosclerosis, peripheral arterial disease, and thrombotic or thromboembolic symptoms or consequences associated with and/or caused by one or more of the following: thromboembolic stroke (including that resulting from atrial fibrillation or from ventricular or aortic mural thrombus), venous thrombosis (including deep vein thrombosis), arterial thrombosis, cerebral thrombosis, pulmonary embolism, cerebral embolism, thrombophilia (e.g., Factor V Leiden, and homocystinenimia), coagulation syndromes and coagulopathies (e.g., disseminated intravascular coagulation), restenosis (e.g., following arterial injury induced endogenously or exogenously), atrial fibrillation, and ventricular enlargement (including dilated cardiac myopathy and heart failure). The compounds of the invention also may be used to treat symptoms or consequences of atherosclerotic diseases and disorders, such as atherosclerotic vascular disease, atherosclerotic plaque rupture, atherosclerotic plaque formation, transplant atherosclerosis, and vascular remodeling atherosclerosis. The compounds of the invention further may be used to treat symptoms or consequences of thrombotic or thromboembolic conditions associated with cancer, surgery, inflammation, systematic infection, artificial surfaces (such as stents, blood oxygenators, shunts, vascular access ports, vascular grafts, artificial valves, etc.), interventional cardiology such as percutaneous transluminal coronary angioplasty (PTCA), immobility, medication (such as oral contraceptives, hormome replacement therapy, and heparin), pregnancy and fetal loss, and diabetic complications including retinopathy, nephropathy, and neuropathy.

The compounds of the present invention may be used for the preservation of tissue, for example, the preservation of tissue as relates to organ transplantation and surgical manipulation. The compounds may be used to treat diseases or disorders in other tissues or muscles that are associated with ischemic conditions and/or to enhance the strength or stability of tissue and muscles. For example, the compounds may be used to treat muscle cell damage and necrosis and/or to enhance athletes' performance.

Additional diseases and disorders that may be treated with the inventive compounds include irritable bowel syndrome, leukemia, CNS disorders associated with cerebral ischemia, such as cerebral infarction, cerebral edema and the like, and diseases associated with proliferation of smooth muscle cells, mesangial cells, and fibroblasts. Such diseases include renal fibrosis, hepatic fibrosis, prostate hypertrophy, and pulmonary fibrosis.

The inventive compounds also may be used to treat veterinary viral infections, such as lentivirus infections, including, but not limited to, equine infectious anemia virus; or retro virus infections, including feline immunodeficiency virus, bovine immunodeficiency virus, and canine immunodeficiency virus.

When the terms "p38 associated condition" or "p38 associated disease or disorder" are used herein, each is intended to encompass all of the conditions identified above as if repeated at length, as well as any other condition that is modulated by p38 kinase activity.

The present invention thus provides methods for treating such conditions, comprising administering to a subject in need thereof an effective amount of at least one compound of Formula (I), or a pharmaceutically-acceptable salt, hydrate, or prodrug thereof The methods of treating p38 kinase-associated conditions may comprise administering compounds of Formula (I) alone or in combination with each other and/or other suitable therapeutic agents such as anti-inflammatory drugs, antibiotics, anti-viral agents, anti-oxidants, cholesterol/lipid lowering agents, anti-tumor agents including antiproliferative agents, and agents used to treat ischemia.

Examples of suitable other anti-inflammatory agents with which the inventive compounds may be used include aspirin, cromolyn, nedocromil, theophylline, zileuton, zafirlukast, monteleukast, pranleukast, indomethacin, and lipoxygenase inhibitors; non-steroidal antiinflammatory drugs (NSAIDs) (such as ibuprofen and naproxin); TNF-α inhibitors (such as tenidap and rapamycin or derivatives thereof), or TNF-α antagonists (e.g., infliximab, enbrel, D2E7, OR1384), cytokine modulators (e.g. TNF-alpha converting enzyme [TACE] inhibitors, Interleukin-1 converting enzyme (ICE) inhibitors, Interleukin-1 receptor antagonists), prednisone, dexamethasone, Enbrel®, cyclooxygenase inhibitors (i.e., COX-1 and/or COX-2 inhibitors such as Naproxen®, Celebrex®, or Vioxx®), CTLA4-Ig agonists/antagonists (LEA29Y), CD40 ligand antagonists, IMPDH inhibitors (such as mycophenolate [CellCept®] and VX-497), integrin antagonists, alpha-4 beta-7 integrin antagonists, cell adhesion inhibitors, interferon gamma antagonists, ICAM-1, prostaglandin synthesis inhibitors, budesonide, clofazimine, CNI-1493, CD4 antagonists (e.g., priliximab), other p38 mitogen-activated protein kinase inhibitors, protein tyrosine kinase (PTK) inhibitors, IKK inhibitors, therapies for the treatment of irritable bowel syndrome (e.g., Zelmac®, Zelnorm®, and Maxi-K® openers such as those disclosed in U.S. Pat. No. 6,184,231 B1), or other NF-κB inhibitors (such calphostin, CSAIDs, and quinoxalines as disclosed in U.S. Pat. No. 4,200,750); corticosteroids (such as beclomethasone, triamcinolone, budesonide, fluticasone, flunisolide, dexamethasone, prednisone, and dexamethasone); disassociated steroids; chemokine receptor modulators (including CCR1, CCR2, CCR3, CCR4, and CXCR2 receptor antagonists); secretory and cytosolic phospholipase A2 inhibitors, VLA4 antagonists, glucocorticoids, salicylates, nitric oxide, and other immunosuppressants; and nuclear translocation inhibitors, such as deoxyspergualin (DSG).

To treat pain, the inventive compounds may be used in combination with aspirin, NSAIDs, or with 5-HT 1 receptor agonists such as buspirone, sumitriptan, eletriptan or rizatriptan.

Examples of suitable antibiotics with which the inventive compounds may be used include β-lactams (e.g., penicillins, cephalosporins and carbopenams); β-lactam and lactamase inhibitors (e.g., augamentin); aminoglycosides (e.g. tobramycin and streptomycin); macrolides (e.g. erythromycin and azithromycin); quinolones (e.g., cipro and tequin); peptides and deptopeptides (e.g. vancomycin, synercid and daptomycin) metabolite-based anti-biotics (e.g., sulfonamides and trimethoprim); polyring systems (e.g., tetracyclins and rifampins); protein synthesis inhibitors (e.g. zyvox, chlorophenicol, clindamycin, etc.); and nitro-class antibiotics (e.g. nitrofurans and nitroimidazoles).

Examples of suitable antiviral agents for use with the inventive compounds include nucleoside-based inhibitors, protease-based inhibitors, and viral-assembly inhibitors.

Examples of suitable anti-osteoporosis agents for use in combination with the compounds of the present invention include alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors.

Examples of suitable anti-oxidants for use in combination with the compounds of the present invention include lipid peroxidation inhibitors such as probucol, BO-653, Vitamin A, Vitamin E, AGI-1067, and α-lipoic acid.

A further use of the compounds of this invention is in combination with steriodal or non-steroidal progesterone receptor agonists ("PRA"), such as levonorgestrel, medroxyprogesterone acetate (MPA).

The inventive compounds also may be used in combination with anti-diabetic agents, such as biguanides (e.g. metformin), glucosidase inhibitors (e.g. acarbose), insulins (including insulin secretagogues or insulin sensitizers), meglitinides (e.g. repaglinide), sulfonylureas (e.g., glimepiride, glyburide and glipizide), biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), glucagon phosphorylase, and dipeptidyl peptidase IV (DP4) inhibitors.

In addition, the compounds may be used with agents that increase the levels of cAMP or cGMP in cells for a therapeutic benefit. For example, the compounds of the invention may have advantageous effects when used in combination with phosphodiesterase inhibitors, including PDE1 inhibitors (such as those described in Journal of Medicinal Chemistry, Vol. 40, pp. 2196-2210 [1997]), PDE2 inhibitors, PDE3 inhibitors (such as revizinone, pimobendan, or olprinone), PDE4 inhibitors (such as rolipram, cilomilast, or piclamilast), PDE7 inhibitors, or other PDE inhibitors such as dipyridamole, cilostazol, sildenafil, denbutyline, theophylline (1,2-dimethylxanthine), ARIFLO™ (i.e., cis-4-cyano-4-[3-(cyclopentyloxy)-4-methoxyphenyl]cyclohexane-1-carboxylic acid), arofyline, roflumilast, C-11294A, CDC-801, BAY-19-8004, cipamfylline, SCH351591, YM-976, PD-189659, mesiopram, pumafentrine, CDC-998, IC-485, and KW-4490.

The inventive compounds may also be useful in combination with anticancer strategies and chemotherapies such as taxol and/or cisplatin. The compounds may be used in conjunction with antitumor agents such as paclitaxel, adriamycin, epithilones, cisplatin, and carboplatin.

In view of their usefulness in treating ischemia, the inventive compounds may be used in combination with agents for inhibiting $F_1F_0$-ATPase, including efrapeptin, oligomycin, autovertin B, azide, and compounds described in U.S. patent application Ser. No. 10/315,818, filed Dec. 10, 2001 and assigned to the present assignee; -alpha- or beta-adrenergic blockers (such as propranolol, nadolol, carvedilol, and prazosin), or -β-adrenergic agonists (such as albuterol, terbutaline, formoterol, salmeterol, bitolterol, pilbuterol, and fenoterol); antianginal agents such as nitrates, for example, sodium nitrates, nitroglycerin, isosorbide mononitrate, isosorbide dinitrate, and nitrovasodilators; antiarrhythmic agents including Class I agents (such as propafenone); Class II agents (propranolol); Class III agents (such as sotalol, dofetilide, amiodarone, azimilide and ibutilide); Class IV agents (such as diltiazem and verapamil); K⁺ channel modulators such as $I_{Ach}$ inhibitors and inhibitors of the $K_v1$ subfamily of K⁺ channel openers such as $I_{Kur}$ inhibitors (e.g., compounds disclosed in U.S. application Ser. No. 09/729,731, filed Dec. 5, 2000); and gap-junction modulators such as connexions; anticoagulant or antithrombotic agents including aspirin, warfarin, ximelagtran, low molecular weight heparins (such as lovenox, enoxaparain, and dalteparin), anti-platelet agents such as GPIIb/GPIIIa blockers, (e.g., abciximab, eptifibatide, and tirofiban), thromboxane receptor antagonists (e.g., ifetroban), P2Y$_1$ and P2Y$_{12}$ antagonists (e.g., clopidogrel, ticlopidine, CS-747, and aspirin/clopidogrel combinations), and Factor Xa inhibitors (e.g., fondaprinux); and diuretics such as sodium-hydrogen exchange inhibitors, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, and amiloride.

Additionally, the inventive compounds may be used in combination with lipid profile modulators and antiatherosclerotic agents including HMG-CoA reductase inhibitors (e.g., pravastatin, simvastatin, atorvastatin, fluvastatin, cerivastatin, AZ4522, itavastatin [Nissan/Kowa]), ZD-4522 (a.k.a. rosuvastatin, atavastatin or visastatin), pravachol, squalene synthetase inhibitors, fibrates, bile acid sequestrants (such as questran), niacin and niacin/statin combinations, lipooxygenase inhibitors, ileal Na$^+$/bile acid cotransporter inhibitors, ACAT1 inhibitors, ACAT2 inhibitors, dual ACAT1/2 inhibitors, microsomal triglyceride transport protein inhibitors (such as disclosed in U.S. Pat. Nos. 5,739,135, 5,712,279 and 5,760,246), cholesterol absorption inhibitors (such as Zetia®), cholesterol ester transfer protein inhibitors (e.g., CP-529414), PPAR-delta agonists, PPAR-alpha agonists, dual PPAR-alpha/delta agonists, LXR-alpha agonists, LXR-beta agonists, LXR dual alpha/beta agonists, and SCAP modulators.

The combination of the inventive compounds with other therapeutic agents may prove to have additive and synergistic effects. The combination may be advantageous to increase the efficacy of the administration or decrease the dosage to reduce possible side-effects.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The present invention also provides pharmaceutical compositions capable of treating p38-kinase associated conditions, including TNF-α, IL-1, and/or IL-8 mediated conditions, as described above. The inventive compositions may contain other therapeutic agents as described above. Pharmaceutical compositions may be formulated by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulations.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g. with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g. CARBOPOL 934®) Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of p38 enzyme levels.

Compounds of within the scope of formula (I) may be tested for activity as inhibitors of p38α/β enzymes and TNF-α using the assays described below, or variations thereof that are within the level ordinary skill in the art. Compounds described in the examples herein have shown surprisingly advantageous activity as kinase inhibitors, particularly inhibitors of p38α/β enzymes.

Biological Assays

Generation of p38 Kinases cDNAs of human p38α, β and γ isozymes are cloned by PCR. These cDNAs can be subcloned in the pGEX expression vector (Pharmacia). GST-p38 fusion protein is expressed in *E. Coli* and purified from bacterial pellets by affinity chromatography using glutathione agarose. p38 fusion protein is activated by incubating with constitutively active MKK6. Active p38 is separated from MKK6 by affinity chromatography. Constitutively active MKK6 is generated according to Raingeaud et al. [*Mol. Cell. Biol.*, 1247-1255 (1996)].

TNF-α Production by LPS-Stimulated PBMCs

Heparinized human whole blood is obtained from healthy volunteers. Peripheral blood mononuclear cells (PBMCs) are purified from human whole blood by Ficoll-Hypaque density gradient centrifugation and resuspended at a concentration of $5 \times 10^6$/ml in assay medium (RPMI medium containing 10% fetal bovine serum). 50 ul of cell suspension is incubated with 50 ul of test compound (4× concentration in assay medium containing 0.2% DMSO) in 96-well tissue culture plates for 5 minutes at RT. 100 ul of LPS (200 ng/ml stock) is then added to the cell suspension and the plate is incubated for 6 hours at 37° C. Following incubation, the culture medium is collected and stored at −20° C. TNF-α concentration in the medium is quantified using a standard ELISA kit (Pharmingen-San Diego, Calif.). Concentrations of TNF-α and $IC_{50}$ values for test compounds (concentration of compound that inhibited LPS-stimulated TNF-α production by 50%) are calculated by linear regression analysis.

p38 Assay

The assays are performed in V-bottomed 96-well plates. The final assay volume is 60 μl prepared from three 20 μl additions of enzyme, substrates (MBP and ATP) and test compounds in assay buffer (50 mM Tris pH 7.5, 10 mM $MgCl_2$, 50 mM NaCl and 1 mM DTT). Bacterially expressed, activated p38 is pre-incubated with test compounds for 10 min. prior to initiation of reaction with substrates. The reaction is incubated at 25° C. for 45 min. and terminated by adding 5 μl of 0.5 M EDTA to each sample. The reaction mixture is aspirated onto a pre-wet filtermat using a Skatron Micro96 Cell Harvester (Skatron, Inc.), then washed with PBS. The filtermat is then dried in a microwave oven for 1 min., treated with MeltilLex A scintillation wax (Wallac), and counted on a Microbeta scintillation counter Model 1450 (Wallac). Inhibition data are analyzed by nonlinear least-squares regression using Prizm (GraphPadSoftware). The final concentration of reagents in the assays are ATP, 1 μM; [γ-$^{33}$P]ATP, 3 nM,; MBP (Sigma, #M1891), 2 μg/well; p38, 10 nM; and DMSO, 0.3%.

TNF-α Production by LPS-Stimulated Mice

Mice (Balb/c female, 6-8 weeks of age, Harlan Labs; n=8/ treatment group) are injected intraperitoneally with 50 ug/kg lipopolysaccharide (LPS; *E coli* strain 0111:B4, Sigma) suspended in sterile saline. Ninety minutes later, mice are sedated by $CO_2$:$O_2$ inhalation and a blood sample was obtained. Serum is separated and analyzed for TNF-alpha concentrations by commercial ELISA assay per the manufacturer's instructions (R&D Systems, Minneapolis, Minn.).

Test compounds are administered orally at various times before LPS injection. The compounds are dosed either as suspensions or as solutions in various vehicles or solubilizing agents.

Abbreviations

For ease of reference, the following abbreviations are employed herein, including the methods of preparation and Examples that follow:

Ph=phenyl
Bz=benzyl
t-Bu=tertiary butyl
Me=methyl
Et=ethyl
Pr=propyl
n-propyl or n-Pr=straight chain propyl
Iso-P, iPr, iso-Pr=isopropyl
MeOH=methanol
EtOH=ethanol
EtOAc=ethyl acetate
Boc=tert-butyloxycarbonyl
BOP=benzotriazol-1-yloxy-tris(dimethylamino)-phosphonium hexafluorophosphate
DCM=dichloromethane
DCE=1,2-dichloroethane
DIPEA=diisopropylethylamine
DMF=N,N-dimethyl formamide
DMF-DMA=N,N-dimethyl formamide dimethyl acetal
DMSO=dimethyl sulfoxide
DPPA=diphenylphosphoryl azide
EDC or EDCI=1-(3-Dimethylaminopropyl)-3-ethylcarbodiimide hydrochloride
HATU=O-(7-Azabenzotriazol-1-yl-N,N,N',N'-tetramethyluronim hexafluorophosphate
HOBt=1-hydroxybenzotriazole hydrate
IPA=isopropanol (isopropyl alcohol)
KOH=potassium hydroxide
$K_2CO_3$=potassium carbonate
$POCl_3$=phosphorous oxychloride
m-CPBA=m-chloroperbenzoic acid
NaH=sodium hydride
NaOH=sodium hydroxide
p-TsOH=p-toluenesulfonic acid
Pd=palladium
Pd/C=palladium on carbon
TFA=trifluoroacetic acid
THF=tetrahydrofuran
min=minute(s)
h or hr=hour(s)
L=liter
mL=milliliter
μL=microliter
g=gram(s)
mg=milligram(s)
mol=moles
mmol=millimole(s)
meq=milliequivalent RT or rt=room temperature
ret. t.=HPLC retention time (minutes)
sat or sat'd=saturated
aq.=aqueous
TLC=thin layer chromatography
HPLC=high performance liquid chromatography
RP HPLC=reverse phase HPLC
Prep HPLC=preparative reverse phase HPLC
LC/MS=high performance liquid chromatography/mass spectrometry
MS=mass spectrometry
NMR=nuclear magnetic resonance
mp=melting point HPLC Conditions:
YMC S5 ODS 4.6×50 mm Ballistic column, 4 mL/min flow rate, 4 min. linear gradient elution (Start solvent % B=0; Final solvent % B=100), solvent A=10% MeOH/90% $H_2O$/0.2% $H_3PO_4$. Solvent B=90% MeOH /10% $H_2O$/0.2% $H_3PO_4$.

mL/minute. The elution gradient uses 100% of solvent A and gradually increases to 100% of solvent B over the 4 min elution time (solvent A=10% methanol/90% water/0.2% phosphoric acid and solvent B=90% methanol/10% water/0.2% phosphoric acid). Eluted products were detected using a uv detector at a wavelength of 220 nm.

Microwave Chemistry: Microwave reactions were performed using the commercially available Smith Synthesizer from Personal Chemistry. This reactor allows for precise control over reaction temperatures and times and greater than atmospheric pressures.

Methods of Preparation

Compounds of Formula (I) may be prepared according to the following Schemes and the knowledge of one skilled in the art. Variables in the schemes (e.g., Q, $R_2$-$R_{11}$) are as defined in the claims below. Solvents, temperatures, pressures, and other reaction conditions may readily be selected by one of ordinary skill in the art.

Scheme 1

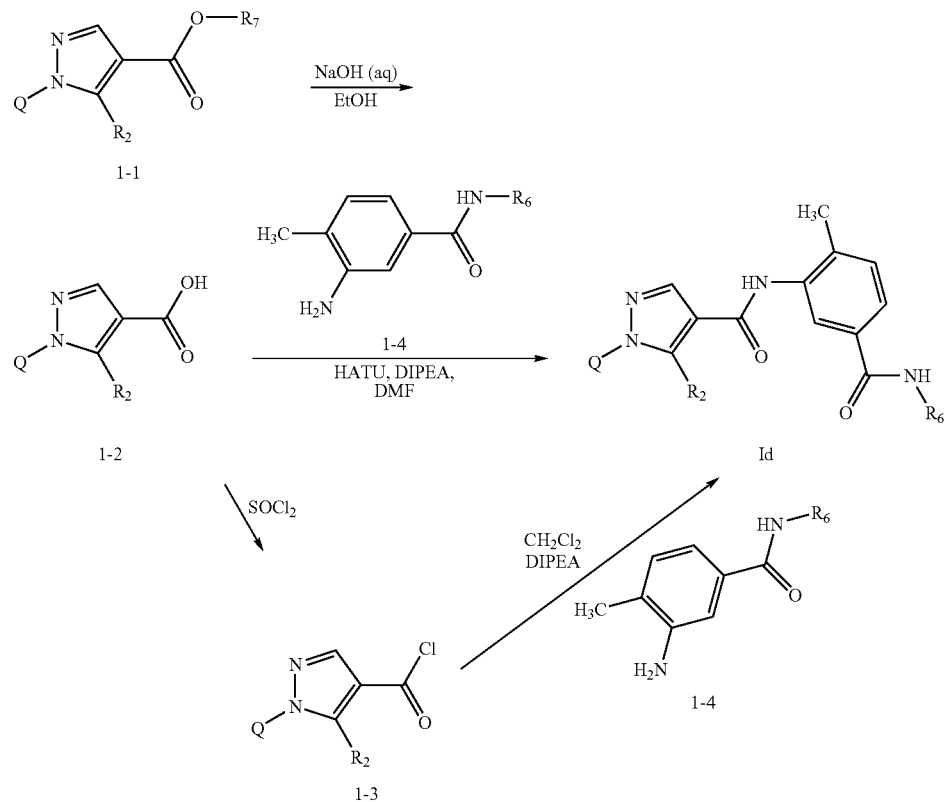

When superscript $^a$ is used, this is intended to refer to the following conditions. Column: Phenomenex 4.6×30 mm; Flow rate: 5 mL/min; Gradient time: 2 min with 1 min hold; Detection wave length: 220 nm; Starting solvent: 10% MeOH-90% H2O-0.1% TFA; and Final solvent: 90% MeOH-10% H2O-0.1% TFA.

For the oxadiazolyl examples (Examples Nos. 82-88), HPLC retention times were determined using a YMC S5 ODS 4.6 mm×50 mm Ballistic chromatography column with a 4 minute total gradient elution time and a flow rate of 4

Compounds of formula (I) having the structure (Id) can be prepared according to Scheme 1. Substituted pyrazoles (1-1) are either commercially available or can be prepared according to literature procedures and/or as described herein. See, e.g., Europ. J. Org. Chem., 17, 2913-2920 (2002); WO 01/46172; Heterocycles, 53, 2775-2780 (2000); J. Heterocyclic Chem., 37, 175-180 (2000); Nippon Kagaku Kaishi, 10, 1144-1147 (1992); Pakistan J. Scientific and Industrial Research, 30, 1-4 (1987); J. Heterocyclic Chem., 16, 657-660 (1979); J. Org. Chem., 21, 1240 (1956); and Joule et. al., Heterocyclic Chemistry, 3d edition, Chapter 22. Each of the foregoing literature references is incorporated herein by reference to the extent they disclose methods for making substituted pyrazoles (1-1) and/or other starting materials and/or reaction conditions useful for making compounds of formula (I) herein.

Hydrolysis of (1-1) gives the corresponding pyrazole acids (1-2), which can be coupled with aniline (1-4) or its salt form (such as HCl) to give compounds (Id) under standard amide coupling conditions. Alternatively, the carboxylic acid moiety of (1-2) can be converted to the acid chloride (1-3), which reacts directly with benzamide (1-4) in solvents such as DCM in the presence of DIPEA (or other bases) to afford (Id). Benzamide compounds may be commercially available and/or can be prepared applying methods described in the literature, or as described below in Schemes 1a and 1b.

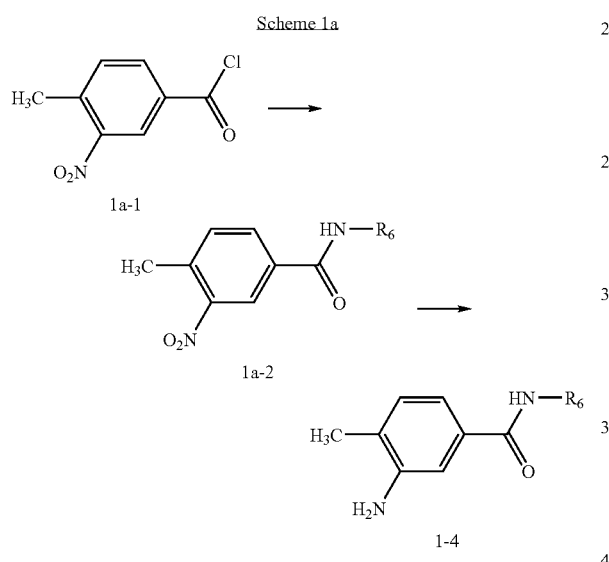

Compound (1-4) can be prepared as outlined in Scheme 1a by 1) reacting a 3-nitro-benzoyl chloride (1a-1) (which is commercially available or can be prepared by one skilled in the art) and an amine $H_2N-R_6$ in $CH_2Cl_2$ to give a nitro intermediate (1a-2); and 2) reducing (1a-2) under conditions such as hydrogen gas and a catalyst in a solvent to afford aniline(1-4). Its salt form can be prepared by reacting (1-4) with an appropriate acid (e.g., HCl).

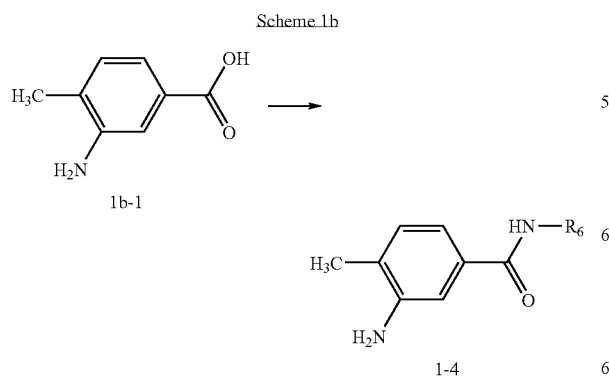

Alternatively, Compound (1-4) can be prepared as outlined in Scheme 1b, by reacting a 3-amino-benzoic acid (1b-1) (which is commercially available or can be prepared by one skilled in the art) with the amine $H_2N-R_6$ in the presence of a coupling agent, such as EDC/HOBt, in a suitable solvent. Its salt form can be prepared by reacting (1-4) with an appropriate acid (e.g., HCl).

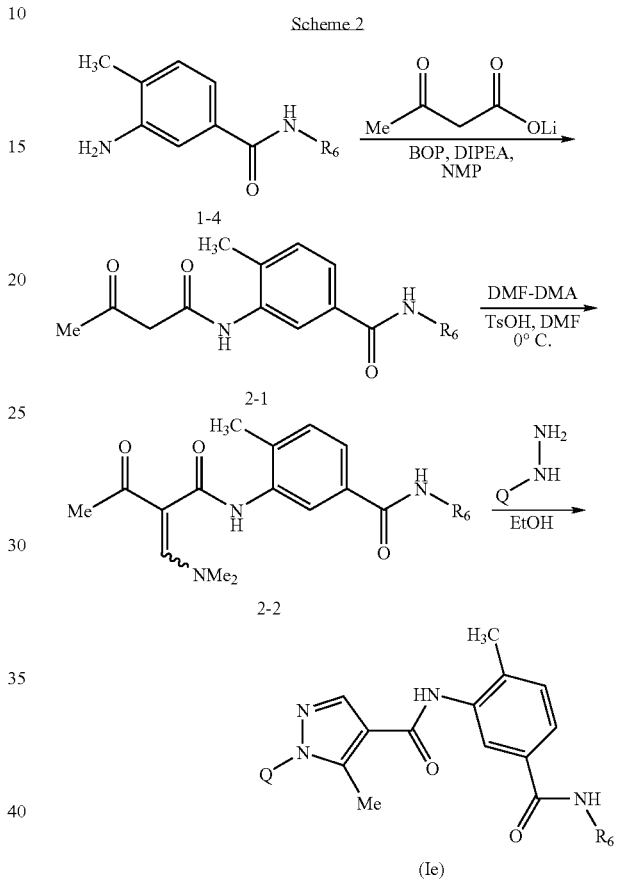

Compounds having the formula (Ie) can be made as shown in Scheme 2. BOP coupling of aniline (1-4) with lithium acetoacetate gives compound (2-1), which can be reacted with DMF-DMA to give compound (2-2). Compound (2-2) can then be reacted with hydrazines to afford compound (Ie).

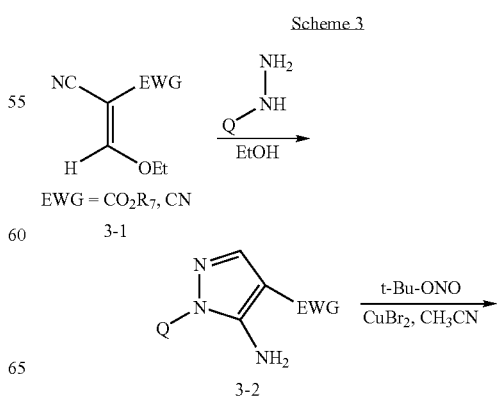

-continued

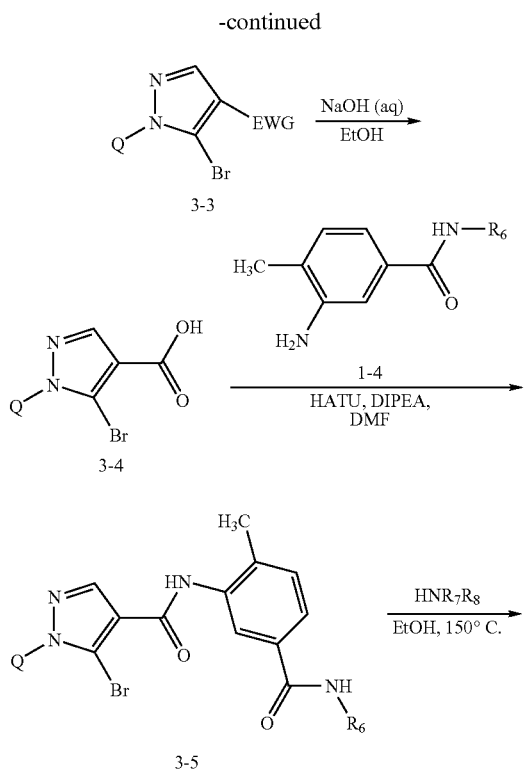

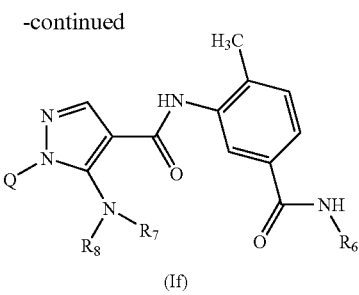

Pyrazoles bearing halo (intermediates), amino, or alkylamino substitution at C5 (the $R_2$ position as recited in the appended claims) can be prepared according to Scheme 3. Reaction of compound (3-1) (such as 2-ethoxymethylene-malononitrile or 2-cyano-3-ethoxy-acrylic acid ethyl ester) with hydrazines gives pyrazoles (3-2), where the C4 position is substituted by a electron withdrawing group (EWG) such as nitrile, methyl or ethyl ester. Conversion of the C5-amino group to the C5-bromo group can be accomplished through reaction with tBuONO and copper (II) bromide. Hydrolysis of the ester or nitrile to the carboxylic acid, followed by amide bond formation, such as through reaction with HATU and the aniline (1-4), gives compound (3-5). Substitution of the bromide with nucleophiles (carbon, oxygen, sulfur, but in particular nitrogen-based nucleophiles) can be accomplished. Reaction of compounds (3-5) with primary or secondary amines in EtOH at elevated temperature and pressure, under microwave irradiation gives amino-substituted pyrazoles (If).

Scheme 4

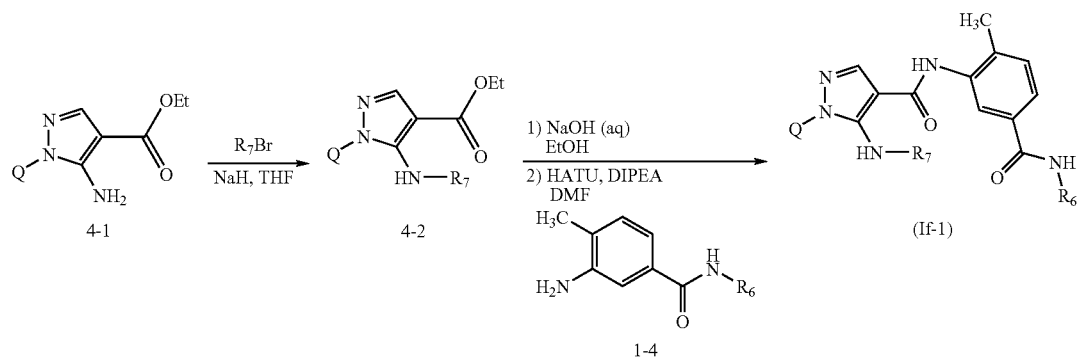

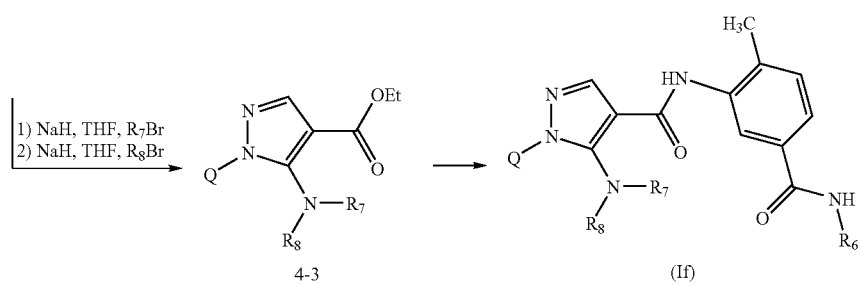

C5-amino substituted pyrazoles can alternately be prepared as shown in Scheme 4. Aminopyrazoles (4-1) (generally prepared according to Scheme 3) can be mono- or bis-alkylated through the reaction with alkyl halides (such as ethyl bromide) in the presence of a suitable base (such as NaH) to afford (4-2) or (4-3). Hydrolysis of the ester, followed by amide bond formation, such as through HATU coupling with (1-4), leads to the C5-alkylamino substituted pyrazoles (If) or (If-1)

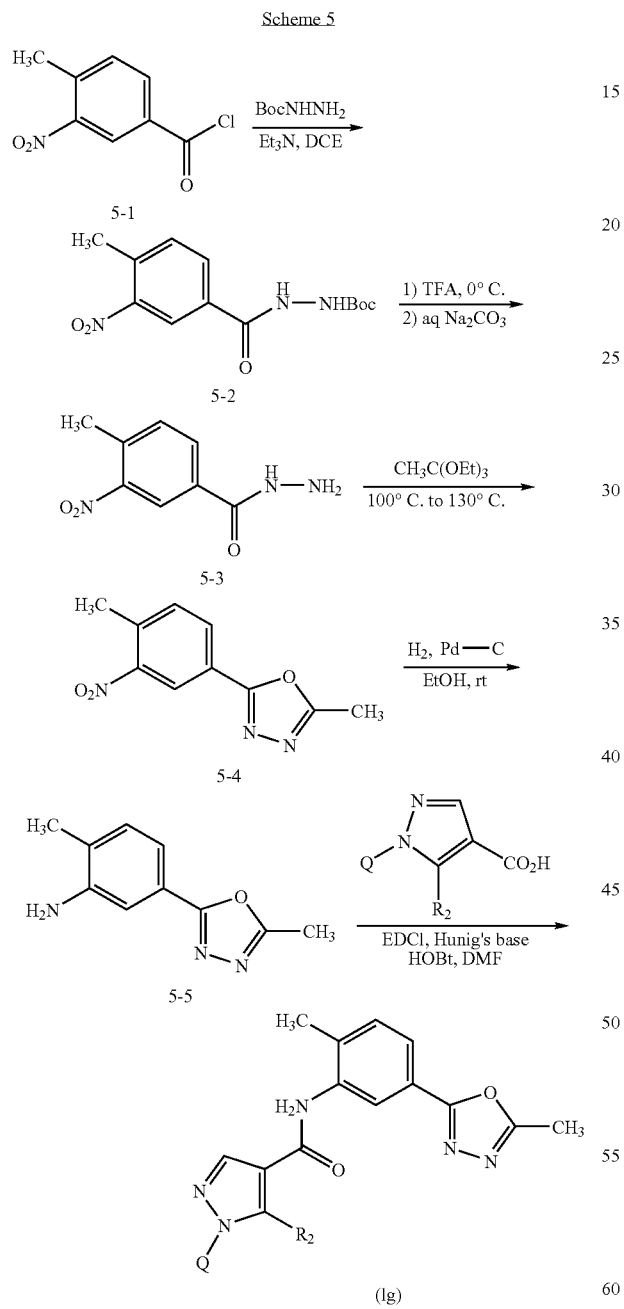

Compounds of formula (Ig) can be prepared from commercially-available compound (5-1) as depicted in Scheme 5. Compound (5-1) can be reacted with tert-butyl carbazate in an organic solvent, such as DCE, in the presence of a base, such as triethylamine, to afford compound (5-2). Compound (5-2) can reacted with an acid, such as TFA, and neutralized with a base, such as aqueous sodium carbonate, to afford compound (5-3). Formation of the oxadiazole can be accomplished by heating compound (5-3) in triethyl orthoacetate to afford compound (5-4) that can be reduced with hydrogen in the presence of a suitable catalyst, such as palladium on carbon, in a solvent, such as EtOH, to afford compound (5-5). Compound (5-5) can then be coupled to carboxylic acid (6) in a solvent such as DMF to provide compound (Ig). It should be understood from the foregoing that in Schemes 1-4 and 6-8 herein, the oxadiazolyl-substituted aniline compound of formula (5-5) can be substituted for the aniline of formula (1-4) and reacted with carboxylic acid pyrazoles, as in Schemes 1, 3 and 4, and/or treated as shown in the Schemes 2 and 8, to provide compounds of formula (I) and/or precursors thereof.

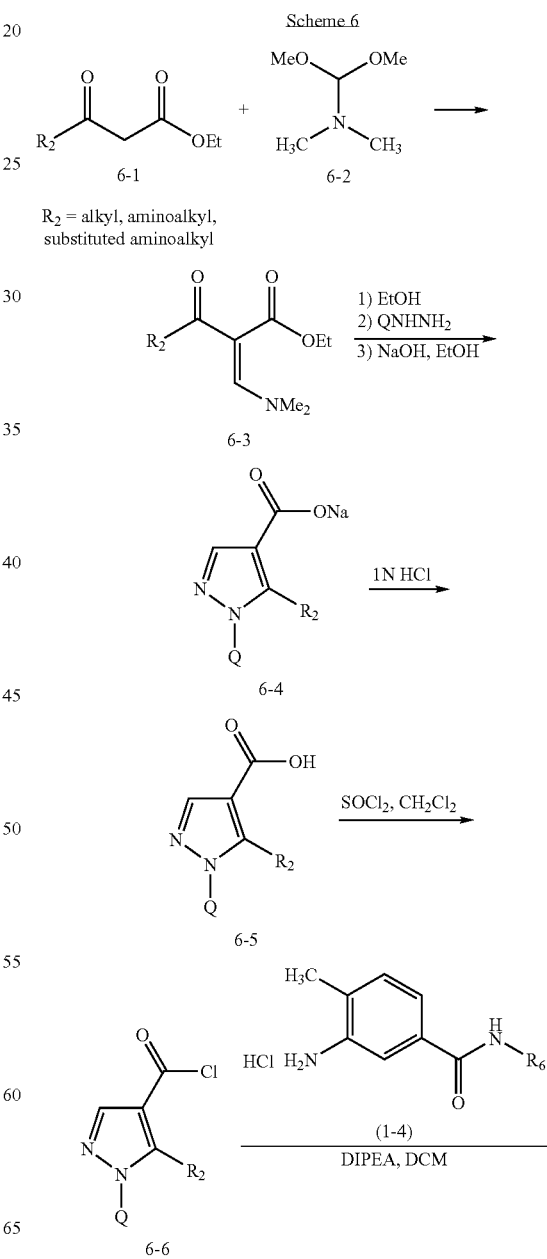

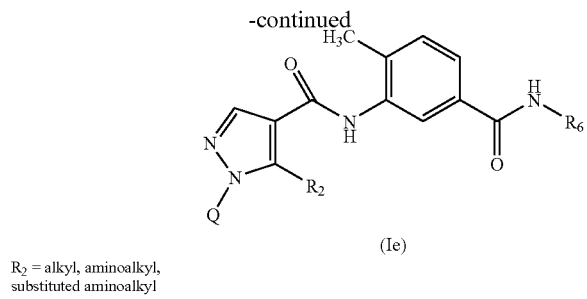

R₂ = alkyl, aminoalkyl, substituted aminoalkyl

Scheme 6 shows a process for making compounds of formula (Ie), wherein R₂ is alkyl, aminoalkyl, or substituted aminoalkyl. Ethylacetoacetate (6-1), for example, ethyl 3-oxobutanoate, can be reacted with methanamine, such as dimethoxy-N—N-dimethylmethanamine (6-2) in solvent to provide intermediate compound (6-3), which when reacted with an appropriate hydrazine, such as, for example, phenylhydrazine, pyridylhydrazine, etc., followed by addition of sodium hydroxide, provides intermediate sodium salt of formula (6-4). Reaction of sodium salt with acid such as HCl provides carboxylic acid of formula (6-5). The carboxylic acid can then be converted to the acid chloride upon reaction with sulfuryl chloride (see also scheme 1), in solvents such as DCM to provide compounds (6-6), which react with benzamide hydrochloride (1-4) (or alternatively compounds 5-5 as in scheme 5), in solvents such as DCM in the presence of base such as DIPEA to provide compounds having the formula (Ie). (See also Examples 11-12, infra).

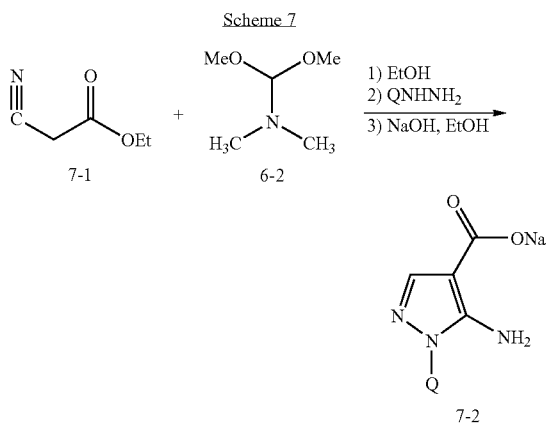

Scheme 7 reflects an alternate process following the general schematic of Scheme 6, but wherein R₂ is a directly-linked amine group, i.e., cyano compound 7-1 is reacted with methanamine, such as dimethoxy-N—N-dimethylmethanamine (6-2) in solvent, followed by an appropriate hydrazine, such as, for example, phenylhydrazine, pyridylhydrazine, etc., in solvent, such as ethanol, followed by addition of sodium hydroxide, to provides intermediate sodium salt of formula (7-2). The amino group of compound (7-2) which can be further elaborated to an alkylamine or substituted amine group R₂, applying principles known in the field, and/or compound (7-2) can be incorporated into other schemes and processes disclosed herein. One skilled in the field will appreciate whether use of amine-protecting groups for the amine of compound (7-2) may be appropriate given other reagents.

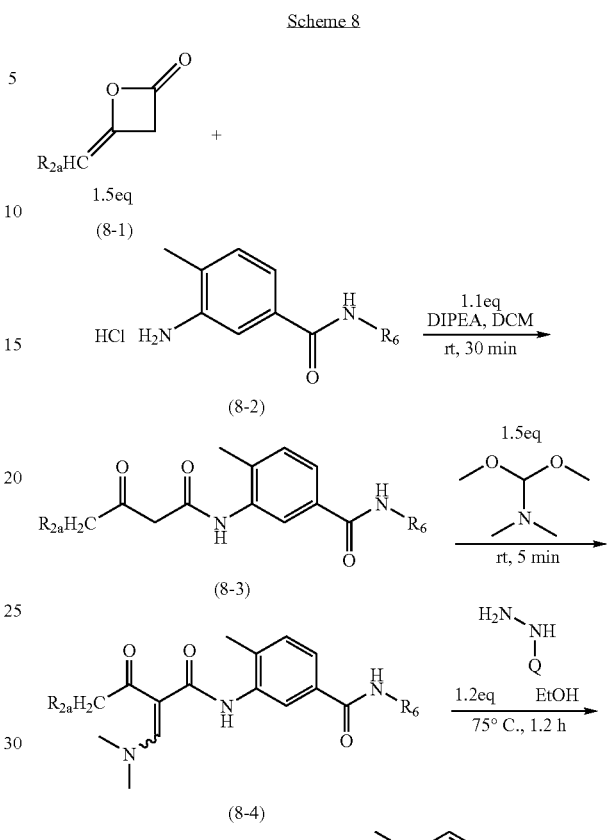

Diketene (8-1), wherein $R_{2a}$ is hydrogen, alkyl, cycloamino, aminoalkyl (preferably wherein $R_{2a}$ is hydrogen), and 3-amino-N-cyclopropyl-4-methylbenzamide hydrochloride can be reacted with DIPEA in DCM at RT to provide compounds (8-3). Addition of DMF-DMA at RT and removal of DCM provides compounds (8-4), which upon reaction with appropriate hydrazine (QNHNH₂), such as optionally-substituted phenylhydrazine, pyridylhydrazine, etc., in solvent such as EtOH, provides compounds of formula (Ih) wherein $R_{2a}$ is as defined above, preferably hydrogen.

In addition, other compounds of formula (I) may be prepared using procedures generally known to those skilled in the art. In particular, the following examples provide additional methods for the preparation of the compounds of this invention. The invention will now be further described by the following working examples, which are non-limiting exemplary embodiments of the invention. HPLC purifications were done on C18 reverse phase (RP) columns using water MeOH mixtures and TFA as buffer solution. These examples are illustrative rather than limiting. There may be other embodiments that fall within the spirit and scope of the invention as defined by the appended claims.

EXAMPLE 1

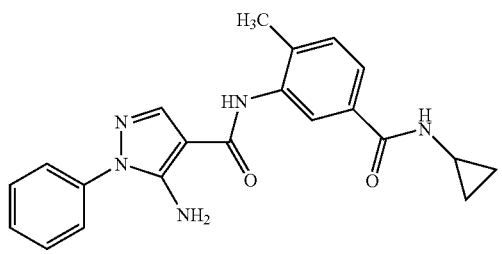

Step A:

5-Amino-1-phenyl-pyrazole-4-carboxylic acid chloride

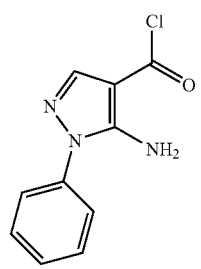
(1A)

A suspension of 5-amino-1-phenyl-pyrazole-4-carboxylic acid (1.27 g, 6.24 mmol) in thionyl chloride (10 mL) was stirred at rt for 1.75 h. The mixture was concentrated under reduced pressure and dried in vacuo to obtain the above acid chloride 1A (1.38 g, 100% yield) as a yellow solid.

Step B:

Compound 1A (40 mg, 0. 15 mmol) was added to a stirred solution of 3-cyclopropylcarboxamido-6-methylaniline (36 mg, 0. 19 mmol) in DCM (1.5 mL) and pyridine (100 µL) at 0° C. The cooling bath was removed after addition and the solution was stirred at rt for 15 min. The reaction mixture was concentrated and the residue was diluted with 0.5 N aq. HCl solution (8 mL). The precipitate was sonicated for several min and filtered. The solid was washed with 0.5 N aq. HCl solution, satd. aq. NaHCO₃ solution, water and dried in vacuo to obtain Example 1 (61 mg, 90% yield) as a white solid. LC/MS : 376.13 (M+H)⁺.

EXAMPLE 2

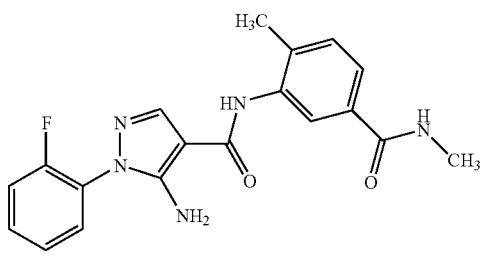

Step A:

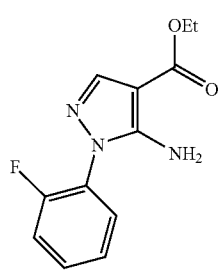
(2A)

Ethyl(ethoxymethylene)-cyanoacetate (2.24 g, 13.3 mmol) was added in portions to a stirred suspension of 2-fluorophenylhydrazine hydrochloride (1.96 g, 12.05 mmol) and triethyl amine (1.68 mL, 12.05 mmol) in absolute EtOH (16 mL). The mixture was stirred for 50 min, diluted with water and extracted with EtOAc. The organic extracts were combined, washed with water, brine, dried (Na2SO4), filtered, and concentrated under reduced pressure and in vacuo to obtain the above compound 2A (3.06 g, quantitative yield) as a light tan solid. HPLC retention time: 1.34 min. LC/MS: 250.13 (M+H)⁺.

Step B:

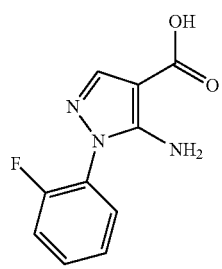
(2B)

A solution of ethyl-5-amino-1-(2-fluorophenyl)-pyrazole-4-carboxylate 2A (3.06 g, 12.28 mmol) in THF:MeOH (64 mL, 1:1) and 2.5 N aq. NaOH solution (31 mL) was heated to 60° C. for 8 h. The mixture was concentrated under reduced pressure and acidified with 6 N aq. HCl solution at 0° C. The precipitated solid was collected by filtration, washed with water and DCM, and dried to obtain the acid 2B (1.72 g, 63%). Additional acid 2B (160 mg, 6%) can be obtained from the filtrate by extractive work up with DCM. HPLC retention time: 0.85ᵃ min. LC/MS: 222.08 (M+H)⁺.

Step C:

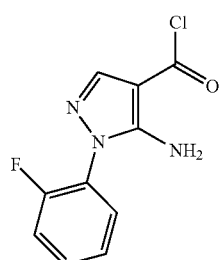
(2C)

A solution of carboxylic acid 2B (0.5 g, 2.26 mmol) in thionyl chloride (3.7 mL) was stirred at rt for 2 h. The mixture was concentrated under reduced pressure and in vacuo to obtain the acid chloride 2C (624 mg, 100% yield) as an orange solid. HPLC retention time: 1.11$^a$ min.; LC/MS: 236.11 (M+H)$^+$ for the corresponding methyl ester.

Step D:

5-Amino-1-(2-fluorophenyl)-pyrazole-4-carboxylic acid chloride 2C (40 mg, 0.14 mmol) was added to a stirred solution of 3-methylcarboxamido-6-methylaniline (31 mg, 0.19 mmol) in DCM (1.5 mL) and pyridine (100 µL) at 0° C. The cooling bath was removed after addition and the solution was stirred at rt for 45 min. The reaction mixture was concentrated and the residue was diluted with 0.5 N aq. HCl solution (8 mL). The precipitated solid was sonicated for several min and filtered. The solid was washed with 0.5 N aq. HCl solution, satd. aq. NaHCO$_3$ solution, water and dried in vacuo to obtain the above Example 2 (33 mg, 65% yield) as a light tan powder. HPLC retention time: 1.20$^a$ min. LC/MS : 368.16 (M+H)$^+$.

EXAMPLE 3

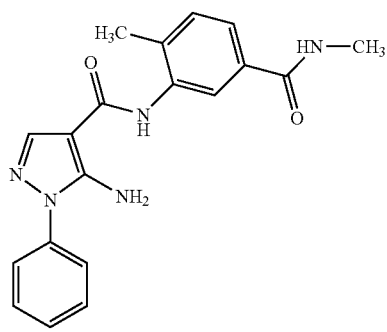

Step A:

5-amino-1-phenyl-4-carboethoxypyrazole

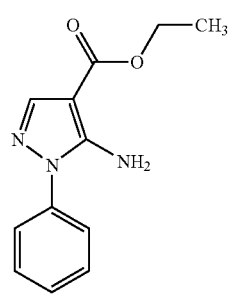

(3A)

Phenyl hydrazine (21.2 gm, 0.19 moles), ethyl (ethoxymethylene)-cyanoacetate (35 gm 0.21 moles), and absolute EtOH (200 ml.) were refluxed 1 hr. The reaction volume was reduced by one-half and cooled in ice, and the desired product was collected by filtration. The filtrate volume was further reduced to 120 ml, cooled, and then filtered to collect additional solids. The yellow solids were combined to provide compound 3A (41.6 gm, 94% yield)

Step B:

5-amino-phenylpyrazole-4-carboxylic acid

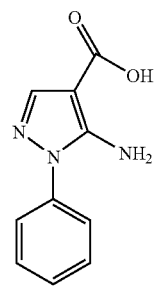

(3B)

Compound 3A (41 gm), THF (50 ml), MeOH (150 ml), and 3N NaOH (100 ml) were combined and refluxed 4 hrs. Most of solvent was removed by evaporation and the remainder was neutralized with 1 N HCl (300 ml). The cream colored solid product was collected by filtration, washed, and dried to give compound 3B (38 gm, quantitative yield).

Step C:

Example 3

Compound 3B (7.42 gm, 36.8 mmole), thionyl chloride (5.22 gm, 1.2 eq), THF (50 ml) and DMF (10 drops) were refluxed briefly. The cloudy reaction solution was filtered through a medium glass frit, evaporated, and the residue was triturated with 9:1 hexanes: diethyl ether (30 ml) to yield a yellow solid product. This was redissolved into THF (100 ml) and was slowly added to a second reaction solution containing 3-amino-4-methyl methylbenzamide (6.0 gm) and pyridine (5.78 gm, 2 eq) in THF at 0 deg C. The reaction was allowed to stir overnight, during which time it came to rt. Reaction was evaporated and the solid residue was washed with 1 N HCl (2×50 ml), 1 N NaOH (2×50 ml), and dried to yield the above Example 3 (10.2 gm, 79.8% yield). (M+H)$^+$=350.13, HPLC ret. time=1.24$^a$.

EXAMPLE 4

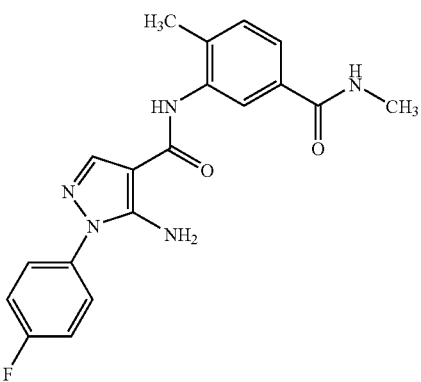

Step A:

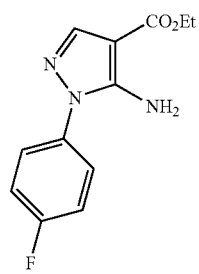

(4A)

Ethyl(ethoxymethylene)cyanoacetate (17.2 g, 101 mmol) and 4-fluorophenylhydrazine hydrochloride (15 g, 92 mmol) were mixed in absolute EtOH (150 mL) at RT and triethylamine (13 mL, 92 mmol) was introduced via syringe dropwise. The mixture was stirred overnight, diluted with ether and filtered. The filtrate was diluted with EtOAc (500 mL) and washed with water (100 mL×3), brine, dried over $Na_2SO_4$, filtered, and concentrated under reduced pressure to obtain 22.5 g (98%) of compound 4A as a brown oil. HPLC ret time: 2.73 min.(broad). LC/MS: 250.48 $(M+H)^-$.

Step B:

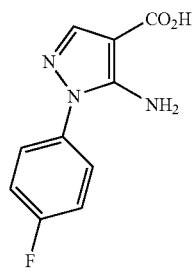

(4B)

A solution of compound 4A (22.5 g, 90.4 mmol) in absolute EtOH (200 mL1) and 3 N aq. NaOH solution (75 mL, 226 mmol) was refluxed for 2 h. The mixture was concentrated under reduced pressure and taken up in water (200 mL) and washed with DCM (100 mL×3). The aqueous layer was acidified with 6 N aq. HCl solution at 0° C., and the precipitated solid was collected by filtration, washed with water, and dried to obtain acid 4B (11.6 g, 58%). HPLC retention time: 1.92 min. LC/MS: 222.08 $(M+H)^+$.

Step C:
Example 4
To a slurry of carboxylic acid (5.5 g, 24.9 mmol) in DCM was added thionyl chloride (2.35 mL, 32.3 mmol). After 10 min, DMF (3 drops) was added, then the solution stirred at RT for 2 h. The mixture was concentrated under reduced pressure to obtain a yellow solid. The solid was slurried in DCM (50 mL) and cooled to 0° C. whereupon 3-methylcarboxamido-6-methylaniline (5.11 g, 31.1 mmol) was added as a solid followed by a dropwise addition of a solution of pyridine (6.0 mL, 74.7 mmol) in DCM (25 mL) over 15 min. After the addition was complete, the cooling bath was removed and the solution was stirred at rt for 30 min. The reaction mixture was concentrated and the residue was treated with water (20 mL) and 1N aq. HCl (50 mL). The resulting slurry was sonicated for several minutes, filtered, and washed with 1 N aq. HCl solution, water and dried in vacuo to obtain approx. 9 g of a yellow solid. The solid was triturated with hot EtOAc, hot ether, then washed with acetonitrile and decolorized in MeOH using charcoal. The filtrate was concentrated and the resulting solid was recrystallized from MeOH/acetonitrile to afford the above Example 4 as a white solid (6.27 g, 69% yield). HPLC retention time: 2.58 min. LC/MS: 368.24 $(M+H)^+$. $^1$H NMR: ($d_6$-DMSO, 500 mHz) δ 9.38 (s, 1 H), 8.37 (m,1 H), 8.11 (s, 1 H), 7.79 (s, 1H), 7.59-7.60 (dd, 2H), 7.59 (s, 1H), 7.35 (s, 1H), 7.31-7.38 (dd, 2H), 6.42 (s, 2 H), 2.76 (d, 3H), 2.26 (s, 3H).

EXAMPLES 5 to 9

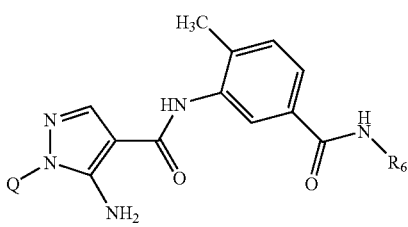

Examples 5 to 9, having the above formula wherein the variables Q and $R_6$ have the values reported in shown in Table 1 were prepared following the procedure described in the preparation of Examples 1 through 4. The starting materials are either commercially available, can be prepared according to the Schemes herein, or applying procedures known in the field.

TABLE 1

| Ex. # | Q | $R_6$ | $(M + H)^+$ | HPLC Retention time (min) |
|---|---|---|---|---|
| 5 | 2-pyridyl | —$CH_3$ | 351.10 | 1.36$^a$ |
| 6 | 2-pyridyl | cyclopropyl-C(CH3)- | 377.10 | 1.47$^a$ |
| 7 | 2-fluorophenyl | cyclopropyl-C(CH3)- | 394.24 | 1.30$^a$ |
| 8 | 4-fluorophenyl | cyclopropyl-C(CH3)- | 394.17 | 1.39$^a$ |

TABLE 1-continued

| Ex. # | Q | R$_6$ | (M + H)$^+$ | HPLC Retention time (min) |
|---|---|---|---|---|
| 9 | 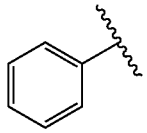 | —CH$_3$ | 364.19 | 1.32$^a$ |

EXAMPLE 10

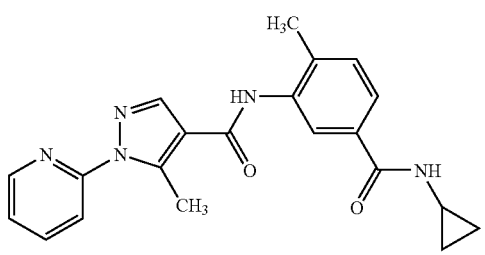

Step A:

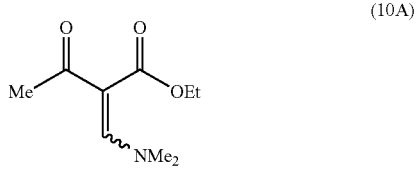
(10A)

To ethyl acetoacetate (100 g, 769 mmol) was added p-TsOH (333 mg, 1.75 mmol) and DMF-DMA (153 mL, 1150 mmol). The solution was heated at 100° C. for 2.5 hr, then cooled to RT. A distillation apparatus was attached and the product was purified by fractional distillation under vacuum to give (10A) (92.7 g, 66%) as a yellow oil.

Step B:

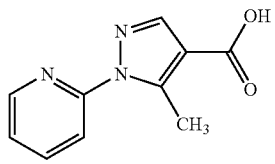
(10B)

To a solution of (10A) (0.424 g, 2.3 mmol) in EtOH (5 mL) was added pyridin-2-yl-hydrazine (0.25 g, 2.3 mmol). The solution was heated to 65° C. for 3 h, then aq NaOH (1 N, 6.9 mL, 6.9 mmol) was added and the reaction was allowed to cool to RT overnight. The EtOH was evaporated and the resulting aqueous solution was acidified to approximately pH 3. The resulting precipitate was collected by filtration and allowed to air dry, affording (10B) as a light tan solid (0.38 g, 81%) HPLC ret. t. (min): 1.92, MW: 203.2, LCMS[M+H]$^+$=204.0.

Step C:

To a solution of (10B) (0.041 g, 0.201 mmol) in NMP (1.0 mL) was added BOP (0.117 g, 0.265 mmol), DIPEA (0.115 mL, 0.66 mmol), and 3-amino-N-cyclopropyl-4-methyl-benzamide hydrochloride (0.050 g, 0.22 mmol). The solution was heated to 50° C. and allowed to stir overnight. The reaction was heated to 80° C. for an additional 4 hr. The solution was cooled to RT and water (2 mL) was added. The product was extracted with EtOAc to afford a crude residue that was further purified by Prep HPLC to afford (10) as an off-white solid (0.032 g, 42%). HPLC ret. t. (min): 3.02, MW: 375.4, LCMS[M+H]$^+$=376.1.

EXAMPLE 10A

Alternate Preparation for Compound of Example 10

1-(2-pyridyl)-5-methylpyrazole-4-carboxylic acid (1.6 gm, 7.9 mmol) and thionyl chloride (10 ml) were stirred at RT for 1 hr. The reaction was evaporated and the residue was redissolved into THF (75 ml). To this was added a solution containing 3-amino-4-methylcyclopropylbenzamide (1.64 gm, 1.1 eq.) and THF (25 ml), and the reaction was stirred overnight at rt. The reaction was evaporated, partitioned between 9:1 methylene chloride:MeOH (100 ml) and 1 N NaOH (2×50 ml), then 1 N HCl (2×50 ml), dried over sodium sulfate, filtered, evaporated and chromatographed (silica gel, 97.5 methylene chloride: 2.5 MeOH) to yield the pure product of Example 10 as a white solid (233 mg).

EXAMPLE 11

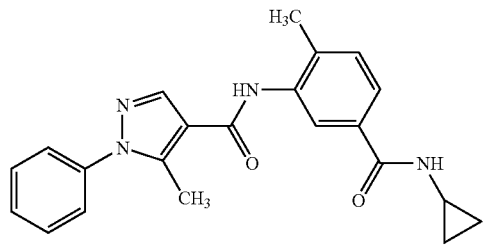

Step A:

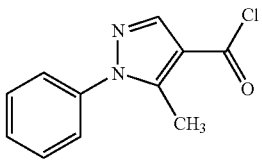
(11A)

5-Methyl-1-phenyl-1H-pyrazole-4-carboxylic acid (0.10 g, 0.495 mmol) [prepared in a fashion similar to that of (10B)] was dissolved in SOCl$_2$ (2 mL) at RT. After stirring at RT for 30 min., the SOCl$_2$ was evaporated, leaving behind the product (11A) as a white solid which was used directly without further purification.

Step B

To a solution of compound (11A) in DCM (2 mL) was added DIPEA (0.345 mL, 1.98 mmol), and 3-amino-N-cyclopropyl-4-methyl-benzamide hydrochloride (0.123 g, 0.544 mmol). The reaction was stirred at RT overnight. Water (4 mL) was added to quench the reaction and the aqueous phase was extracted with DCM (3×3 mL). After evaporation, the organic residue was purified by Prep HPLC to afford the above Example (11) as a white solid (0.139 g, 75%). HPLC ret. t. (min): 2.87, MW: 374.5, LCMS[M+H]+=375.2.

EXAMPLE 11A

Alternate Procedure to Make Example 11

Step A:

Sodium 5-methyl-1-phenyl-1H-pyrazole-4-carboxylate (11A-2)

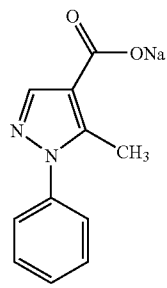

A solution of ethyl 3-oxobutanoate (130.14 g, 1 mol) and dimethoxy-N,N-dimethylmethanamine (119.16 g, 1 mol) in EtOH (200 mL) was stirred at 60° C. for 1 h, then cooled to RT. Phenylhydrazine (98.33 mL, 1 mol) was added to the solution and the temperature was kept under 60° C. After the addition was completed, the mixture was stirred at 60° C. for 1 h. The EtOH was removed under reduced pressure and the residue was dissolved in EtOAc (1 L), then washed with 1N HCl (50 mL), NaHCO₃ (100 mL), H₂O and brine. The organic solvent was removed under reduced pressure and the residue was dissolved in EtOH (460 mL). An aqueous solution (100 mL) of NaOH (80 g) was added and the mixture was stirred at 65° C. for 2 h. After the solution was cooled to RT, the precipitate was collected with filtration and washed with isopropyl alcohol to give the above white sodium salt. Yield 81%, 1HNMR (CD3OD): 7.94 (s, 1H), 7.45-7.59 (m. 5H), 2.53 (s, 3H).

Step B:

5-Methyl-1-phenyl-1H-pyrazole-4-carboxylic acid (11B-2)

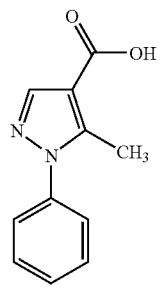

The salt from Step A (11A-2) iwas stirred in 1N HCl (500 ml) solution for 20 min. The precipitate was collected with filtration and dried to give the above acid as a white solid (162 g, 98% yield). 1HNMR (CDCl3): 11.50-12.80 (s, 1H), 8.12 (s, 1H), 7.26-7.54 (m, 5H), 2.59 (s, 3H).

Step C:

5-Methyl-1-phenyl-1H-pyrazole-4-carbonyl chloride (11C-2)

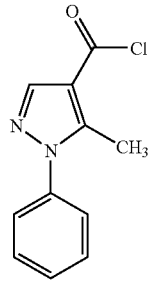

To a solution of 5-methyl-1-phenyl-1H-pyrazole-4-carboxylic acid from Step B (11B-2) (20.2 g, 0.1 mol) in DCM (200 mL) and DMF (730 mg, 0.01 mol) was added sulfuryl dichloride (8.73 mL, 0.12 mol) at RT. The mixture was stirred at 36° C. for 2 h. The solution was concentrated under reduced pressure and DCM (200 mL) was added to the white solid residue to form a suspension of the above corresponding acyl chloride. Yield: 98%, 1HNMR CDCl3): 8.16 (s, 1H), 7.45-7.59 (m, 5H), 2.53 (s, 3H).

Step D:

N-(5-(cyclopropylcarbamoyl)-2-methylphenyl)-5-methyl-1-phenyl-1H-pyrazole-4-carboxamide (Example 11)

To a solution of 3-amino-N-cyclopropyl-4-methylbenzamide hydrochloride?? (22.6 g, 0.1 mol) in DCM (300 mL) was added DIPEA (41.9 mL, 0.24 mol). The solution was stirred for 5 min., then cooled to 0° C. and the suspension from Step B was added. The mixture was stirred for 2 h at RT and quenched with water (200 mL). The precipitate was collected and washed with water and DCM, then stirred in EtOH (100 mL) and water (100 mL). The solid was collected and washed with 50% EtOH in water and further purified by recrystallization in 95% EtOH to give Example 11 as white solid (95% yield). $^1$H NMR(500 MHz, DMSO) δ: 0.52 (d, 2H, J=1.7), 0.62 (m, 2H), 2.23 (s, 3H), 2.49 (s, 3H), 2.80 (m, 1H), 7.28 (d, 1H, J=7.7), 7.50 (m, 5H), 7.57 (d, 1H, J=7.7), 7.76 (s, 1H), 8.26 (s, 1H), 8.36 (s, 1H), 9.59 (s, 1H) $^{13}$NMR (500 MHz, DMSO) δ: 5.59, 11.43, 17.90, 22.94, 115.19, 124.41, 125.20, 125.60, 128.31, 129.18, 129.97, 132.25, 136.08, 137.09, 138.58, 139.27, 142.10, 161.51, 166.81.

EXAMPLE 11B

Alternate Procedure to Make Example 11

To a mixture of 3-amino-N-cyclopropyl-4-methylbenzamide hydrochloride (22.6 g, 0.1 mmol) and DIPEA (19.2 mL, 0.11 mmol) in DCM (200 mL) was added diketene (11.6 mL, 0.15 mmol), and the resulting solution was stirred at RT for 30 min. DMF-DMA (20 mL, 0.15 mol) was added, and the solution was stirred at RT for 5 min. The DCM was removed under reduced pressure. The residue was dissolved in EtOH (100 mL) and phenylhydrazine (11.8 mL, 0.12 mol) was added. The solution was refluxed for 1.2 hour. The precipitate was collected at RT and purified by recrystallization in EtOH (100 mL) to afford Example 11 (28 g) as white crystals in 76% yield. $^1$H NMR (500 MHz, DMSO) δ: 0.52 (d, 2H, J=1.7), 0.62 (m, 2H), 2.23 (s, 3H), 2.49 (s, 3H), 2.80 (m, 1H), 7.28 (d, 1H, J=7.7), 7.50 (m, 5H), 7.57 (d, 1H, J=7.7), 7.76 (s, 1H), 8.26 (s, 1H), 8.36 (s, 1H), 9.59 (s, 1H) $^{13}$C NMR (500 MHz, DMSO) δ:5.59, 11.43, 17.90, 22.94, 115.19, 124.41, 125.20, 125.60, 128.31, 129.18, 129.97, 132.25, 136.08, 137.09, 138.58, 139.27, 142.10, 161.51, 166.81

EXAMPLE 12

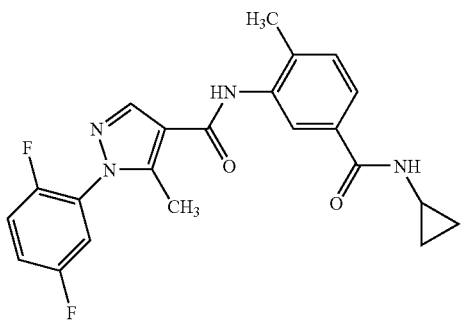

Step A:

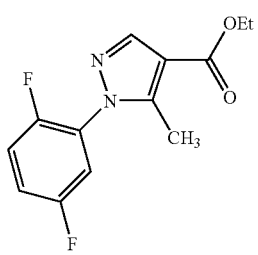
(12A)

To a solution of compound 10A (64.26 g, 0.347 mmol) (see Example 10, above) in EtOH (250 mL) at RT was added 1,5-difluorophenylhydrazine (50 g, 0.347 mmol) in several portions. The exothermic reaction was monitored to prevent the solution from boiling, with the internal temperature reaching 55° C. The reaction was then heated in an oil bath to an internal temperature of 65° C. and stirred overnight. Upon cooling to RT, the EtOH was evaporated and the resulting brown solid was taken up in EtOAc (300 mL) and washed with 1 N HCl (150 mL) and saturated aq. NaHCO$_3$ (150 mL). The two aqueous phases were sequentially back-extracted with EtOAc (50 mL). The combined organic phases were washed with brine (150 mL), dried over Na$_2$SO$_4$, filtered, and concentrated to afford ester 12A as a tan solid.

Step B:

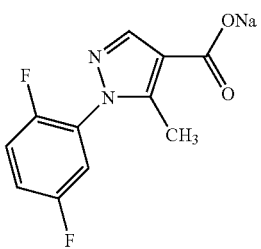
(12B)

The ester 12A was taken up in EtOH (160 mL) and a solution of NaOH (28 g, 0.694 mmol) in water (35 mL) was added. This solution was allowed to stir at RT for 4 days. Reaction was found to be incomplete by HPLC analysis, so the temperature was brought to just below reflux (65-70° C.) for 2-3 h. The reaction was cooled to 0° C. and the resulting solids were collected by filtration. The solids were washed with ice cold IPA until no color eluted. The sodium salt 12B was obtained as an off-white solid (76.14 g, 84.4% over 2 steps). It was allowed to air dry, then used directly in the next step.

Step C:

1-(2,5-difluoro-phenyl)-5-methyl-1H-pyrazole-4-carboxylic acid

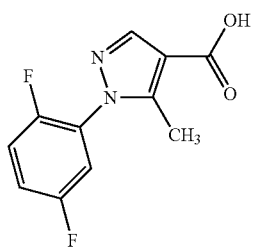
(12C)

The sodium salt 12B (76.1 g) was added in portions to a stirred solution of 1N HCl (500 mL). After 1-2 h the product was collected by filtration and washed with ice cold dilute HCl (0.1 N) to afford 1-(2,5-difluoro-phenyl)-5-methyl-1H-pyrazole-4-carboxylic acid (12C) as a white solid (69.3 g, 99.4%). HPLC retention time: 2.10 min; LCMS MH$^+$=239.09; $^1$HNMR (500 MHz, DMSO-d6) δ 12.56 (s, 1H), 8.01 (s, 1H), 7.60 (m, 2H), 7.52 (m, 1H), 2.38 (s, 1H) ppm.

Step D:

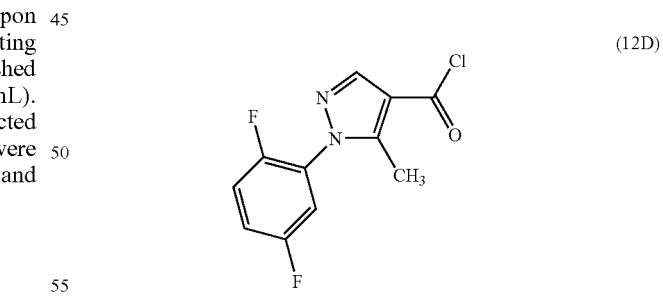
(12D)

To a solution of compound 12C (68 g, 0.285 mmol) and DMF (2.1 mL) in DCM (700 mL) was added SOCl$_2$ (24.9 mL, 0.343 mmol) slowly over 10-15 min. The reaction was stirred at RT overnight then brought to reflux for 1-2 h. Additional SOCl$_2$ (5 mL) was added and heating continued for 4 h. HPLC analysis indicated slight s.m. remaining. Additional SOCl$_2$ (5 mL) and DMF (1 mL) was added and heating continued for 2-3 h. The reaction was concentrated to afford compound 12D as an off-white solid that was used directly for the next reaction.

Step E:

Example 12

Compound 12D was suspended in DCM (1 L) and 3-amino-N-cyclopropyl-4-methyl-benzamide hydrochloride salt (70.94 g, 0.343 mmol) and DIPEA (119.1 mL, 0.654 mmol) were added. The reaction was initially exothermic, causing the solution to boil. After stirring at RT overnight a white precipitate formed. Water (400 ml) was added and the mixture was shaken vigorously. The solids were collected, washed with water (300 mL) and DCM, to give an off-white solid. The solid was dissolved in boiling EtOH (600 mL) and hot water (400 mL) was added along with saturated aq. NaHCO$_3$ (100 mL). After cooling, the resulting precipitate was collected by filtration, washed with ice cold 1:1 EtOH: water to afford the product of Example 12 as a white crystalline solid (93.36 g, 79.8% over 2 steps) HPLC retention time: 2.63 min; LCMS MH$^+$=411.13; HRMS Obs. Mass 411.1641 Calc. Mass 411.1633 Elemental Analysis: Theoretical for $C_{22}H_{20}N_4O_2F_2$: C 64.38, H 4.91, N 13.65, F 9.25 KF: <0.1%, Cl: <0.05% Observed/experimental from test: C 64.17, H 4.77, N 13.64, F 9.37; $^1$HNMR (500 MHz, DMSO-d6) δ 9.69 (s, 1H), 8.39 (d, 4.9 Hz, 1H), 8.36 (s, 1H), 7.80 (s, 1H), 7.63 (m, 3H), 7.55 (m, 1H), 7.35 (d, 7.7 Hz, 1H) 2.86 (m, 1H), 2.42 (s, 3H), 2.28 (s, 3H), 0.68 (m, 2H), 0.69 (m, 2H) ppm. $^{13}$CNMR (500 MHz, DMSO-d6) δ 167.45, 161.86, (159.28, 154.4), (157.34, 152.44), 144.58, 140.77, 137.80, 136.63, 132.93, 130.64, (127.51, 127.43, 127.31), 126.30, 125.16, 118.77 (m, 2C), (117.04, 116.83), 115.86, 23.62, 18.54, 11.16, 6.25 ppm.

EXAMPLES 13-38

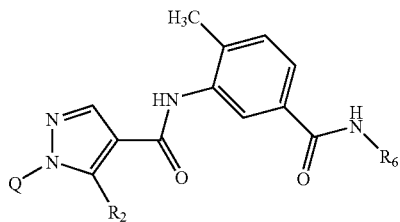

Examples 13-38, having the above formula wherein the variables Q, R$_2$ and R$_6$ have the values reported in shown in Table 2 were prepared following the procedure described in the preparation of Examples 10 through 12. The starting materials are either commercially available or can be prepared according to the Schemes herein and/or applying procedures known in the field.

TABLE 2

| Ex. No. | Q | R$_2$ | R$_6$ | HPLC time (min.) | MS (M$^+$) |
|---|---|---|---|---|---|
| 13 | 3-fluorophenyl | —CH$_3$ | cyclopropyl | 2.72 | 393.2 |
| 14 | 2-fluorophenyl | —CH$_3$ | cyclopropyl | 2.57 | 393.2 |
| 15 | 6-ethoxypyridazin-3-yl | —CH$_3$ | cyclopropyl | 2.83 | 421.1 |
| 16 | 3,5-dichloropyridin-4-yl | —CH$_3$ | cyclopropyl | 2.75 | 444.1 |
| 17 | 4-trifluoromethyl-6-methylpyridin-2-yl | —CH$_3$ | cyclopropyl | 3.47 | 458.2 |

TABLE 2-continued

| Ex. No. | Q | R₂ | R₆ | HPLC time (min.) | MS (M⁺) |
|---|---|---|---|---|---|
| 18 | 5-(trifluoromethyl)pyridin-2-yl | —CH₃ | 1-cyclopropyl | 3.36 | 444.2 |
| 19 | pyridin-4-yl | —CH₃ | 1-cyclopropyl | 1.77 | 376.2 |
| 20 | 6-ethoxypyridin-2-yl | —CH₃ | 1-cyclopropyl | 3.28 | 420.1 |
| 21 | 6-methylpyridin-2-yl | —CH₃ | 1-cyclopropyl | 2.75 | 390.2 |
| 22 | 3-chloropyridin-2-yl | —CH₃ | 1-cyclopropyl | 2.51 | 410.1 |
| 23 | 3-(trifluoromethyl)pyridin-2-yl | —CH₃ | 1-cyclopropyl | 2.65 | 444.2 |
| 24 | 2-ethylphenyl | —CH₃ | 1-cyclopropyl | 3.58 | 403.1 |
| 25 | 4-methylphenyl | —CH₃ | 1-cyclopropyl | 3.54 | 389.1 |
| 26 | 3-methylphenyl | —CH₃ | 1-cyclopropyl | 3.52 | 389.1 |

TABLE 2-continued

| Ex. No. | Q | $R_2$ | $R_6$ | HPLC time (min.) | MS (M+) |
|---|---|---|---|---|---|
| 27 | 2-methylphenyl | —CH$_3$ | cyclopropyl | 3.42 | 389.1 |
| 28 | phenyl | n-propyl | —CH$_3$ | 3.01 | 377.2 |
| 29 | phenyl | n-propyl | cyclopropyl | 3.24 | 403.3 |
| 30 | pyridin-3-yl | —CH$_3$ | cyclopropyl | 2.19 | 376.1 |
| 31 | 3-(methylsulfonyl)phenyl | —CH$_3$ | cyclopropyl | 2.37 | 453.1 |
| 32 | 2-(methylsulfonyl)phenyl | —CH$_3$ | cyclopropyl | 2.42 | 453.2 |
| 33 | 3-cyanopyridin-2-yl | —CH$_3$ | cyclopropyl | 2.16 | 401.2 |
| 34 | 2,6-dichlorophenyl | —CH$_3$ | cyclopropyl | 2.59 | 443.1 |
| 35 | phenyl | n-propyl | n-propyl | 3.20 | 405.1 |

TABLE 2-continued

| Ex. No. | Q | R₂ | R₆ | HPLC time (min.) | MS (M⁺) |
|---|---|---|---|---|---|
| 36 | phenyl | n-propyl | Et | 3.17 | 391.1 |
| 37 | phenyl | n-propyl | —CH₂—CH(CH₃)₂ | 3.45 | 419.3 |
| 38 | phenyl | n-propyl | Iso-Pr | 3.29 | 405.3 |

EXAMPLE 39

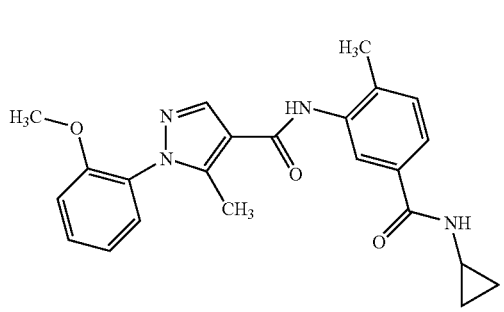

Step A:

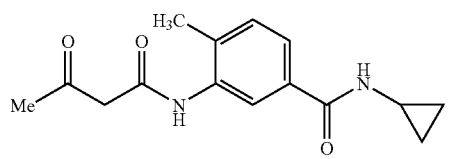
(39A)

To solution of lithium acetoacetate (90%, 0.066 g, 0.611 mmol), BOP (0.270 g, 0.611 mmol), and DIPEA (0.106 mL, 0.611 mmol) in DMF (1 mL) was added 3-amino-N-cyclopropyl-4-methyl-benzamide hydrochloride (0.115 g, 0.51 mmol). The solution was stirred at RT overnight, water (4 mL) was added, and the product extracted with EtOAc. After evaporation, the organic residue was purified by flash chromatography (silica gel, 50-100% EtOAC in hexanes) to afford (39A) as a white semi-solid (0.049 g, 35%). HPLC ret. t. (min): 1.69, MW: 274.3, LCMS[M+H]⁺=275.1.

Step B:

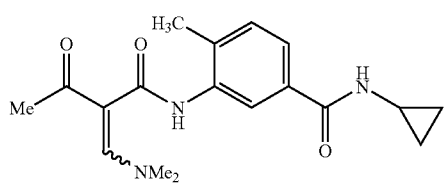
(39B)

To a solution of (39A) (0.050 g, 0.18 mmol) in DMF (0.5 mL) was added DMF-DMA (2 mL) and p-TsOH (0.005 g). The reaction was stirred at RT for 2 hr, then the excess DMF-DMA was evaporated under reduced pressure. The resulting DMF solution of (39B) was used for subsequent reactions without further purification.

Step C:

To the crude DMF solution of (39B) was added EtOH (1 mL) and 2-methoxyphenylhydrazine (0.377 g, 2.73 mmol). The solution was stirred at RT for 45 min, then heated to 60° C. for 1.5 hr. Purification by Prep HPLC afforded the above Example 39 as a light tan solid (0.0085 g, 12%). HPLC ret. t. (min): 2.79, MW: 404.5, LCMS[M+H]⁺=405.2.

EXAMPLES 40-51

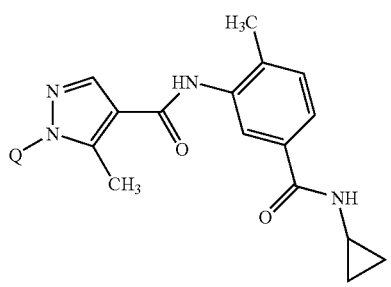

Examples 40-51, having the above formula wherein the variable Q has the values reported in shown in Table 3, were prepared following the procedure described in the preparation of Example 39. Starting materials are either commercially available or can be prepared according to the Schemes herein and/or applying procedures known in the field.

TABLE 3

| Ex. No. | Structure | HPLC time (min.) | MS (M+) |
|---|---|---|---|
| 40 | 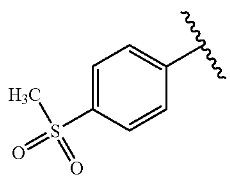 | 2.41 | 453.3 |
| 41 | 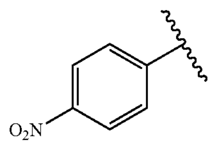 | 2.86 | 420.2 |
| 42 | 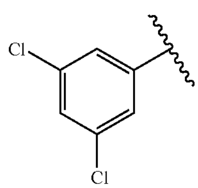 | 3.50 | 443.1 |
| 43 | 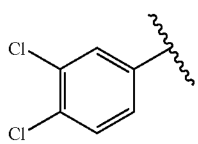 | 3.43 | 443.2 |
| 44 | 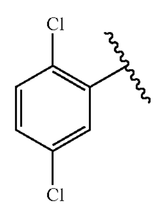 | 3.14 | 443.2 |
| 45 | 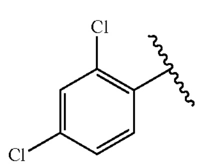 | 3.24 | 443.2 |
| 46 | 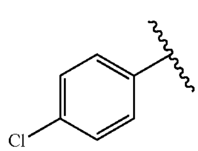 | 3.13 | 409.2 |
| 47 | 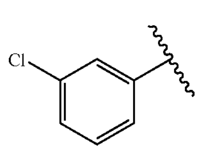 | 3.16 | 409.2 |
| 48 | | 2.92 | 409.2 |
| 49 | | 2.93 | 405.3 |
| 50 | | 2.86 | 420.2 |
| 51 | | 2.67 | 393.0 |

EXAMPLE 52

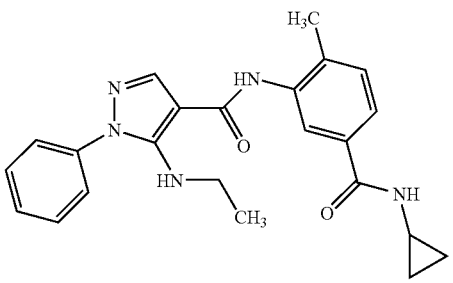

Step A:

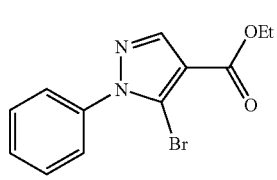

(52A)

To a solution 5-amino-1-phenyl-1H-pyrazole-4-carboxylic acid ethyl ester (0.25 g, 1.05 mmol) and copper (II) bromide (0.281 g, 1.26 mmol) in acetonitrile (2 mL) at 0° C. was added tert-butylnitrite (0.167 mL, 1.26 mmol) dropwise. The reaction was warmed to RT over 2 hr, then stirred overnight at RT. The reaction was layered with EtOAC (8 mL) and washed with 1N aq. HCl (2×3 mL), water (1×3 mL), brine (1×3 mL). The organic phase was dried over MgSO₄, filtered, and evaporated to afford (52A) as a yellow solid (0.304 g, 98%, 85% AP HPLC). HPLC ret. t. (min): 3.62, MW: 295.13, LCMS[M+H]$^+$=295.3.

Step B:

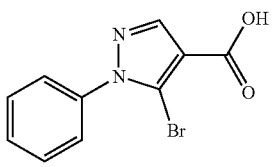
(52B)

To a solution of compound (52A) (0.025 g, 0.085 mmol) in THF (1 mL) at 0° C. was added aq. NaOH (1 N, 0.25 mL, 0.25 mmol). The solution was warmed to RT overnight, then heated to 50° C. for 3-4 hr. The THF was evaporated and the aqueous solution was acidified to approximately pH 3. The resulting precipitate was collected by filtration and allowed to air dry, affording (52B) as an off-white solid (0.015 g, 64%) HPLC ret. t. (min): 2.54, LCMS[M+H]$^+$=267.1, 269.1.

Step C:

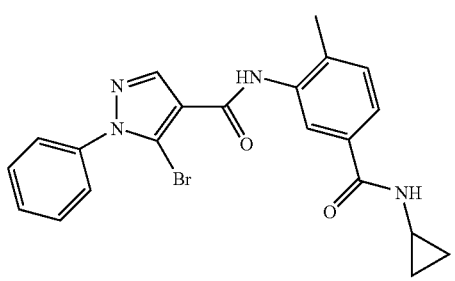
(52C)

To a solution of (52B) (0.109 g, 0.41 mmol) in DMF (2 mL) was added HATU (0.233 g, 0.613 mmol), DIPEA (0.276 mL, 1.52 mmol), and 3-amino-N-cyclopropyl-4-methyl-benzamide hydrochloride (0. 12 g, 0.530 mmol). The solution was stirred at 65° C. for 4 hr. After cooling to RT, water (8 mL) was added and the resulting precipitate was collected by filtration and allowed to air dry to afford 52C as a tan solid (0.112 g, 63%). HPLC ret. t. (min): 2.92, MW: 439.3, LCMS[M+H]$^+$=439.1.

Step D:

To a solution of (52C) (0.020 g, 0.455 mmol) in EtOH (1 mL) was added an excess of ethylamine (70 wt. % in H$_2$O, 1 mL). The solution was placed in a Personal Chemistry Smith Synthesize Microwave reactor vial, capped with a pressure cap, and heated in the automated Microwave Reactor at 150° C. for 2 h. The solvent was evaporated and the residue purified by Prep HPLC to afford Example 52 (0.0098 g, 53%) as an off-white solid. HPLC ret. t. (min): 3.59, MW: 403.5, LCMS [M+H]$^+$=404.2.

EXAMPLES 53-74

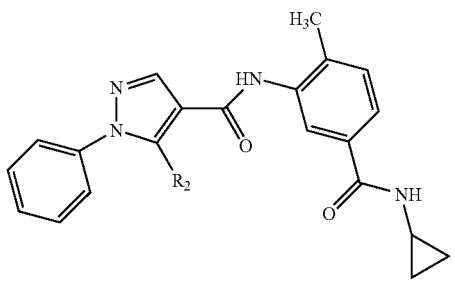

Examples 53-74, having the above formula wherein the variable R$_2$ has the values reported in shown in Table 4, were prepared following the procedure described in the preparation of Example 52. Starting materials are either commercially available or can be prepared according to the Schemes herein and/or applying procedures known in the field.

TABLE 4

| Ex. No. | R$_2$ | HPLC time (min.) | MS (M$^+$) |
|---|---|---|---|
| 53 | (HN-CH$_2$-CH(OH)-CH$_3$) | 2.55 | 434.3 |
| 54 | (HN-CH$_2$-CH(OH)-CH$_3$, opposite stereo) | 2.56 | 434.2 |
| 55 | (NH-CH$_2$-4-pyridyl) | 1.81 | 467.3 |
| 56 | (NH-CH$_2$-tetrahydrofuran-2-yl) | 2.88 | 460.3 |
| 57 | (NH-CH$_2$-tetrahydrofuran-2-yl, opposite stereo) | 2.88 | 460.3 |

TABLE 4-continued

| Ex. No. | R₂ | HPLC time (min.) | MS (M⁺) |
|---|---|---|---|
| 58 | HN-CH₂CH₂CH₂-N(CH₃)₂ | 2.26 | 475.3 |
| 59 | N(CH₃)₂ with H₃C | 2.97 | 404.1 |
| 60 | HN-CH₂-CH(OH)-CH₃ | 2.78 | 434.1 |
| 61 | HN-cyclobutyl | 3.40 | 430.3 |
| 62 | HN-CH₂CH₂CH₂-OCH₃ | 3.08 | 448.30 |
| 63 | H₃C-CH(NH-)-CH₂-OCH₃ | 2.92 | 448.3 |
| 64 | HN-CH₂CH₂-OCH₃ | 2.73 | 434.2 |
| 65 | HN-CH₂-CH(CH₃)₂ | 3.47 | 432.3 |

TABLE 4-continued

| Ex. No. | R₂ | HPLC time (min.) | MS (M⁺) |
|---|---|---|---|
| 66 | HN-CH₂CH₂CH₂-(imidazol-1-yl) | 2.11 | 484.3 |
| 67 | HN-CH₂CH₂CH₂-N(CH₃)₂ | 2.09 | 461.3 |
| 68 | NH-CH₂-(tetrahydrofuran-2-yl) | 3.08 | 460.3 |
| 69 | HN-cyclopropyl | 3.19 | 416.2 |
| 70 | NH-CH₂CH₂-morpholin-4-yl | 1.94 | 489.3 |
| 71 | HN-CH₂CH₂-N(CH₃)₂ | 1.93 | 447.3 |
| 72 | N-morpholin-4-yl | 2.84 | 446.3 |

TABLE 4-continued

| Ex. No. | R₂ | HPLC time (min.) | MS (M⁺) |
|---|---|---|---|
| 73 |  | 3.32 | 418.2 |
| 74 |  | 3.75 | 418.2 |

EXAMPLE 75

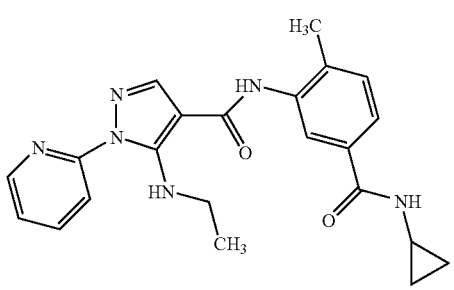

Step A:

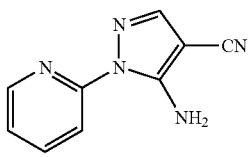
(75A)

To a solution of pyridin-2-yl-hydrazine (5.0 g, 45.9 mmol) in MeOH (30 mL) was added 2-ethoxymethylene-malononitrile (5.5 g, 50.5 mmol) in several portions at RT. The mixture was heated to reflux for 3 h, then cooled to –20° C. and stored overnight. The resulting precipitate was collected by filtration and allowed to air dry, affording (75A) as a yellow solid (7.16 g, 84%) HPLC ret. t. (min): 2.24, MW: 185.2, LCMS[M+H]⁺=186.1.

Step B:

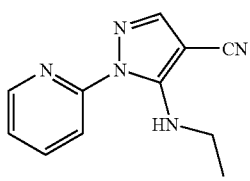
(75B)

To a solution of compound (75A) (2.0 g, 10.7 mmol) in DMF (10 mL) at 0° C. was added NaH (60%, 11.9 g, 11.9 mmol) in portions. Stirring continued until gas evolution had ceased, at which time EtBr (0.888 mL, 11.9 mmol) was added dropwise. Stirring continued for 1 hr. at 0° C., then the reaction was warmed to rt and quenched with water. The resulting precipitate was collected by filtration and air dried to afford (75B) as a yellow solid (1.47 g, 64%). HPLC ret. t. (min): 2.97, MW: 213.2, LCMS[M+H]⁺=214.1.

Step C:

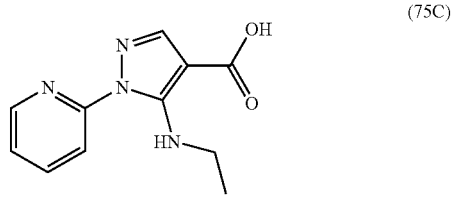
(75C)

A solution of (75B) (1.47 g, 6.9 mmol), MeOH (15 mL), water (10 mL), and aq. NaOH (3 ON, 35 mL) was heated to reflux overnight. The MeOH was acidified and pH of the resulting solution was adjusted to between 3-6. The resulting precipitate was collected by filtration and air dried to afford (75C) as a pale yellow solid (1.19 g, 69%). HPLC ret. t. (min): 2.25, MW: 204.2, LCMS[M+H]⁺=205.2.

Step D:

To a solution of (75C) (0.05 g, 0.22 mmol) in DMF (0.5 mL) was added HATU (0.11 g, 0.29 mmol) and DIPEA (0.122 mL, 0.7 mmol). After stirring at RT for 45 min., 3-amino-N-cyclopropyl-4-methyl-benzamide hydrochloride (0.059 g, 0.26 mmol) was added. The solution was heated to 65° C. and allowed to stir overnight. The reaction was heated to 85° C. for an additional 2 hr. Water (2 mL) was added and the product was extracted with EtOAc to afford a crude residue that was further purified by Prep HPLC to afford (75) as a pale yellow solid (0.023 g, 26%). HPLC ret. t. (min): 2.90, MW: 404.5, LCMS[M+H]⁺=405.1.

EXAMPLE 76

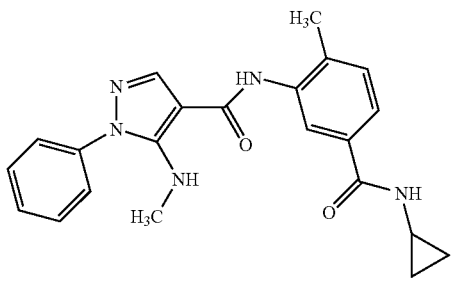

Step A:

Ethyl 5-(methylamino)-1-phenyl-1H-pyrazole-4-carboxylate

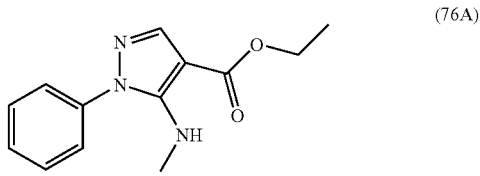
(76A)

To a solution of ethyl 5-amino-1-phenyl-1H-pyrazole-4-carboxylate (15 g, 65 mmol) in DMF (100 mL) at 0° C. was added NaH (60%, 2.85 g, 71.5 mmol) in several portions. After stirring at 0° C. for 1 h, iodomethane (4.45 mL, 71.5 mmol) was added dropwise. The solution was stirred for an additional 2 h at 0° C., then gradually warmed to RT The reaction was quenched with water, resulting in the formation of a white precipitate that was collected by filtration and allowed to air dry. Compound 76A was obtained (11.8 g) and used without further purification. HPLC ret. t. (min): 2.70, MW: 245.3, LCMS[M+H]$^+$=246.3

Step B:

5-(methylamino)-1-phenyl-1H-pyrazole-4-carboxylic acid

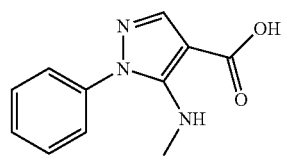

(76B)

A solution of (76A) (11.8 g, 48.2 mmol), EtOH (50 mL), water (50 mL), and aq. NaOH (3N, 48 mL) was heated to reflux overnight. After cooling to 0° C., the solution was carefully acidified with 1N HCl. The resulting precipitate was collected by filtration and air dried to afford compound (76B) as a white solid (10.4 g, 69%). HPLC ret. t. (min): 1.99, MW: 217.2, LCMS[M+H]$^+$=218.3

Step D:

Example 76

To thionyl chloride (40 mL) at RT was added (76B) (0.970 g, 4.47 mmol) in several portions. After stirring at RT for 30 min, the thionyl chloride was evaporated to dryness. The residue was dissolved in DCE (8 mL) and 3-amino-N-cyclopropyl-4-methylbenzamide hydrochloride (1.11 g, 4.91 mmol) followed by DIPEA (2.33 mL, 13.4 mmol) were added. The reaction was allowed to stir at RT for 2 days, then quenched by the addition of water (2 mL) and aq. NaOH (1 N, 2 mL) resulting in the formation of a precipitate. The solution was centrifuged and the aq. layer was removed via pipet. An additional aliquot of water (5 mL) was added, the slurry was stirred for several minutes and again centrifuged. After removal of the aqueous layer, an initial solid was collected by filtration. This solid was slurried in 10% EtOH/90% water at RT for 2-3 h, then collected by filtration and air dried to afford Example 76 as a white solid (0.753 g) HPLC ret. t. (min): 2.68, MW: 389.5, LCMS[M+H]$^+$=390.2

EXAMPLES 77-80

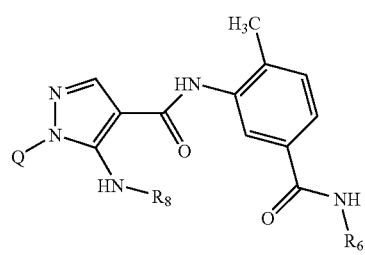

Examples 77-80, having the above formula wherein the variables Q, $R_6$ and $R_8$ have the values reported in shown in Table 5, were prepared following the procedure described in the preparation of Examples 75 and 76. Starting materials are either commercially available or can be prepared according to the Schemes herein, or applying procedures known in the field.

TABLE 5

| Ex. No. | Q | $R_8$ | $R_6$ | HPCL time (min.) | MS (M$^+$) |
|---|---|---|---|---|---|
| 77 | 2-methylphenyl | Et | Et | 2.97 | 406.2 |
| 78 | pyridin-2-yl | Et | Et | 2.63 | 393.2 |
| 79 | phenyl | Et | Et | 2.88 | 392.1 |
| 80 | 2-methylphenyl | Et | cyclopropyl | 3.18 | 418.1 |

EXAMPLE 81

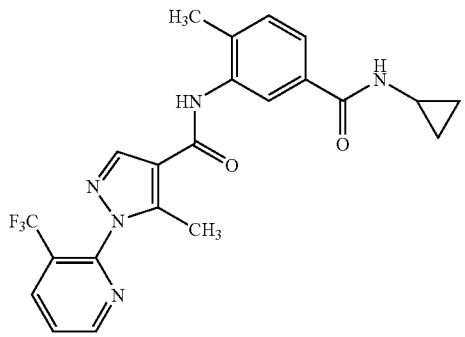

Step A:

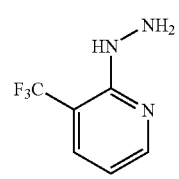

(81A)

A solution of 2-chloro-3-trifluoromethylpyridine (21 g, 116 mmol), hydrazine monohydrate (70 mL), and EtOH (40 mL) was slowly heated to 90° C. and maintained at this temperature for 3 h. After cooling to rt, the mixture was concentrated on a rotary evaporator to afford a thick slurry. This material was dissolved in DCM (350 mL) and the resulting layers were separated. The aqueous layer was extracted with additional DCM (2×75 mL) and the combined organic extracts were washed with water (4×100 mL) and brine (100 mL). After drying over anhyd. sodium sulfate, the extracts were filtered and concentrated in vacuo to afford 16.6 g (81%) of a light grey solid. This material was used without any further purification. HPLC Ret. time: 0.29 min. $^1$H NMR: (CDCl$_3$, 400 mHz) δ 8.33 (d, J=4.8 Hz, 1H), 7.70 (d, J=7.7 Hz, 1H), 6.74 (dd, J=7.5, 5.2 Hz, 1H), 6.26 (br s, 1H), 4.04 (s, 2H).

Step B:

(81B)

A mixture of ethylacetoacetate (100 mL), DMF-DMA (130 mL), and p-toluene sulfonic acid (350 mg) was stirred at 100° C. for 4 h, then allowed to stand at rt for 3 days. Distillation in vacuo yielded 107 g of a yellow liquid. (bp=110-120° C./6 mm Hg). bp (Literature value=265° C./720 mm Hg).

Step C:

(81C)

A solution of compound 81A (16.6 g, 94 mmol) and compound 81B (19.1 g, 103 mmol) in EtOH (250 mL) was heated at reflux for 5 h then cooled to rt. To this mixture was added 3 N aq NaOH (55 mL) and the resulting solution was heated at 85° C. for an additional 3.5 h. After cooling to rt, the EtOH was removed on a rotary evaporator and the mixture was diluted with water to a total volume of ~350 mL. This mixture was extracted with a 9:1 mixture of DCM/methanol (4×100 mL) and the combined extracts were washed with brine (150 mL) and then dried over anhyd. sodium sulfate. Filtration and concentration in vacuo yielded ~24 g of an off-white solid. The solid was dissolved in warm diethyl ether (~350 mL) and concentrated to a volume of ~75 mL. The remaining diethyl ether was decanted away from the solid. This process was repeated 2 more times and the resulting solid was dried in vacuo to afford 20.5 g (81%) of compound 81C as an off-white solid. HPLC Ret. time: 2.13 min. LCMS [M+H]$^+$=272.5. $^1$H NMR: (d$_4$-MeOH, 400 mHz) δ 8.89 (d, J=4.8 Hz, 1H), 8.48 (dd, J=8.0, 1.4 Hz, 1H), 8.04 (s, 1H), 7.87 (dd, J=7.5, 4.4 Hz, 1H), 2.45 (s, 3H).

Step D:

Example 81

To a mixture of compound 81C (10.0 g, 37 mmol) in DCM (70 mL) at rt were successively added DMF (0.29 mL, 3.7 mmol) and thionyl chloride (3.5 mL, 48 mmol) and the resulting solution was stirred at rt for 3 h. Concentration in vacuo afforded 10.7 g of a clear yellow oil. This material was dissolved in DCM (32 mL) and slowly added to a homogeneous mixture of 3-amino-N-cyclopropyl-4-methylbenzamide hydrochloride (10.0 g, 44 mmol) and diisopropylamine (16 mL, 92 mmol) in DCM (70 mL) at 0° C. The resulting mixture was allowed to warm to rt and stir for 16 h. The reaction mixture was diluted with DCM (250 mL) and the solution was successively washed with 0.25 N aq HCl (4×200 mL), water (150 mL), and brine (150 mL), then dried over anhyd. sodium sulfate, filtered, and concentrated in vacuo to afford a pale yellow solid. The solid was triturated 3 times with hot diethyl ether (250 mL) and the resulting solid was dried in vacuo to afford 14 g of an off-white solid. Recrystallization from hot MeOH/water (1:1, 200 mL) afforded 12.6 g (77%) of Example 81 an off-white solid. HPLC Ret. time: 2.76 min. LCMS [M+H]$^+$=476.4. $^1$H NMR: (d$_6$-DMSO, 400 mHz) δ 9.74 (s, 1H), 8.95 (dd, J=4.6, 1.0 Hz, 1H), 8.58 (dd, J=8.0, 1.4 Hz, 1H), 8.41 (d, J=4.2 Hz, 1H), 8.35 (s, 1H), 7.9 (dd, J=7.8, 4.8 Hz, 1H), 7.84 (d, J=1.5 Hz, 1H), 7.65 (dd, J=7.9, 16. Hz, 1H), 7.35 (d, J=8.0 Hz, 1H), 2.90-2.83 (m, 1H), 2.43 (s, 3H), 2.30 (s, 3H), 0.72-0.63 (m, 2H), 0.60-0.56 (m, 2H).

EXAMPLE 82

Step A:

(82A)

To a rt solution of tert-butyl carbazate (2.6 g, 20 mmol) and triethylamine (3.1 mL, 22 mmol) in DCE (100 mL) was added a solution of 4-methyl-3-nitrobenzoyl chloride in DCE (25 mL) over 30 minutes. After the addition was complete the resulting cloudy mixture was stirred at rt for 2 h then the mixture was successively washed with 10% aqueous citric acid (2×75 mL) and brine (100 mL), then dried over anhydrous sodium sulfate. The solution was diluted with EtOAc (100 mL), filtered, and concentrated in vacuo to a volume of approximately 50 mL. The mixture was diluted with hexanes (50 mL) and sonicated for a few minutes, and the resulting precipitated solid was collected by vacuum filtration and dried in vacuo to afford 4.7 g (74%) of compound (82A) as a white solid. HPLC $t_R$=2.54 min. $^1$H NMR (400 MHz, $d_6$-DMSO): δ 10.30 (s, 1H), 8.86 (s, 1H), 8.27 (s, 1H), 7.91 (d, 1H), 7.48 (d, 1H), 2.41 (s, 3H), 1.26 (s, 9H).

Step B:

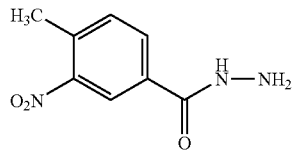

(82B)

Compound 82A (4.4 g, 15 mmol) as a solid was added in portions to trifluoroacetic acid (45 mL) at 0° C. and the mixture was stirred at this temperature for 30 min and at rt for an additional 30 minutes. The mixture was then concentrated in vacuo and the resulting white solid was partitioned between 2N aq sodium carbonate (200 mL) and EtOAc (200 mL). The layers were separated and the aqueous portion extracted with additional EtOAc (5×100 mL), and the combined extracts were washed with brine (100 mL), dried over anhydrous sodium sulfate, filtered, and concentrated in vacuo to yield 2.96 g (99%) of compound (82B) as a white solid. HPLC $t_R$=1.05 min. $^1$H NMR (500 MHz, $d_6$-DMSO): δ 10.20 (br s, 1H), 8.42 (s, 1H), 8.05 (d, 1H), 7.62 (d, 1H), 5.43 (br s, 2H), 2.56 (s, 3H). LCMS $[M+H]^+$=196.3.

Step C:

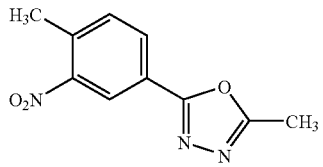

(82C)

A suspension of compound 82B (2.9 g, 15 mmol) in triethyl orthoacetate (50 mL) was heated to 100° C. giving a clear solution. After heating at this temperature for 2 h, the mixture was heated to 130° C. for an additional hour then cooled to rt and heterogeneously concentrated in vacuo. The resulting residue was dissolved in EtOAc (250 mL) and washed with water (100 mL) and brine (75 mL) then dried over anhydrous sodium sulfate, filtered, and concentrated in vacuo to afford 3.2 g of compound 82C as a light yellow solid. HPLC $t_R$=2.45 min. $^1$H NMR (500 MHz, $CDCl_3$): δ 8.57 (s, 1H), 8.16 (d, 1H), 7.49 (d, 1H), 2.66 (s, 3H), 2.63 (s, 3H).

Step D:

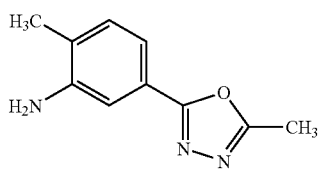

(82D)

To a suspension of compound 82C (0.37 g) in EtOH (40 mL) was added 5% Pd/C (35 mg) and the mixture was allowed to stir under an atmosphere of hydrogen at rt for 2 h. The mixture was filtered through Celite and the resulting clear filtrate was concentrated in vacuo and the residue was triturated with methanol. Filtration and drying of the collected solid afforded 220 mg of compound 82D as an off-white solid. HPLC $t_R$=1.19 min. $^1$H NMR (500 MHz, $d_6$-DMSO): δ 7.23 (s, 1H), 7.08 (d, 1H), 7.05 (d, 1H), 5.22 (s, 2H), 2.53 (s, 3H), 2.10 (s, 3H). LCMS $[M+H]^+$=190.3.

Step E:

Example 82

A mixture of 5-Methyl-1-phenyl-1H-pyrazole-4-carboxylic acid (28 mg, 0.14 mmol), 1-[3-(dimethylamino)propyl]-3-ethylcarbodiimide hydrochloride (33 mg, 0.17 mmol) and 1-hydroxybenzotriazole (23 mg, 0.17 mmol) in anhydrous DMF (0.4 mL) was reacted at rt for 1.5 h. At this time, aniline (82D) was added as solid followed by DIPEA (36 µL, 0.20 mmol). The resulting mixture was then heated at 60° C. for 16 h then the solution was diluted with water (0.4 mL) and allowed to cool to RT. The resulting solids were collected by vacuum filtration and dried in vacuo to afford 33 mg of the title compound as a tan solid. HPLC Ret. Time: 2.78 min. LCMS $MH^+$ (m/z) 374.

EXAMPLES 83-88

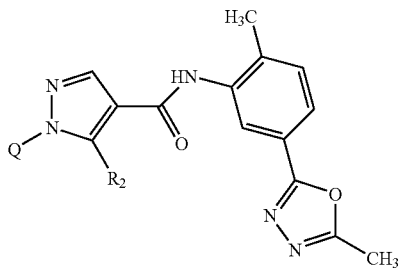

Examples 83-88, having the above formula wherein the variables Q and $R_2$ have the values reported in shown in Table 6, were prepared following the procedure described in the preparation of Example 82. Starting materials are either commercially available, can be prepared according to the Schemes herein, or applying procedures known in the field.

TABLE 6

| Ex. No. | Q | $R_2$ | HPLC Ret. Time (min) | Mass Spec. $M + H^+$ (m/z) |
|---|---|---|---|---|
| 83 | 2-fluorophenyl | $CH_3$ | 2.75 | 392 |

TABLE 6-continued

| Ex. No. | Q | R$_2$ | HPLC Ret. Time (min) | Mass Spec. M + H$^+$ (m/z) |
|---|---|---|---|---|
| 84 | 3-fluorophenyl | CH$_3$ | 2.85 | 392 |
| 85 | 4-fluorophenyl | CH$_3$ | 2.82 | 392 |
| 86 | 2,5-difluorophenyl | CH$_3$ | 2.80 | 410 |
| 87 | 2-pyridyl | CH$_3$ | 2.54 | 375 |
| 88 | phenyl | HN-CH$_3$ | 2.86 | 389 |

We claim:

1. A compound having the formula (I),

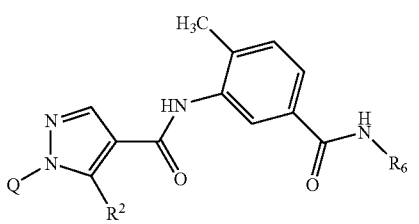

(I)

or a pharmaceutically-acceptable salt, or, stereoisomer thereof wherein:

Q is an optionally-substituted phenyl, pyridazinyl, pyrimidinyl, or pyrazinyl ring;

R$_2$ is selected from C$_{1-6}$alkyl, NR$_7$R$_8$, and C$_{1-6}$alkyl substituted with a group NR$_7$R$_8$;

R$_6$ is C$_{1-6}$alkyl or cyclopropyl;

R$_7$ and R$_8$ are independently selected from hydrogen, C$_{1-6}$alkyl, and C$_{3-6}$cycloalkyl, wherein each of said groups R$_7$ and R$_8$ are in turn optionally substituted with one to two of OH, O(C$_{1-4}$alkyl), imidazolyl, pyridyl, phenyl, tetrahydrofuryl, NH$_2$, NH(C$_{1-4}$alkyl), N(C$_{1-4}$alkyl)$_2$, and N-morpholinyl, or alternatively, R$_7$ and R$_8$ are taken together with the nitrogen atom to which they are attached to form a morpholinyl, piperidinyl, or piperazinyl ring.

2. A compound according to claim 1, or a pharmaceutically-acceptable salt, or stereoisomer, thereof, having the formula,

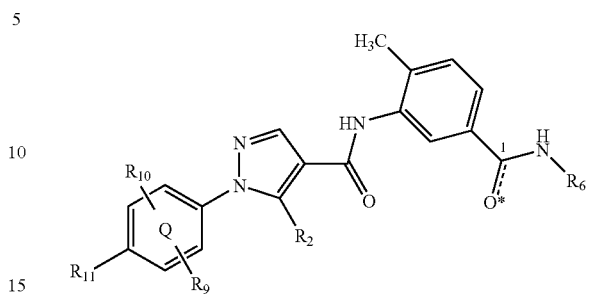

wherein

Q is a phenyl, pyridazinyl, pyrimidinyl, or pyrazinyl ring, and R$_9$, R$_{10}$, and R$_{11}$ are each independently selected from hydrogen, C$_{1-4}$alkyl, O(C$_{1-4}$alkyl), halogen, haloC$_{1-4}$alkyl, cyano, SO$_2$(C$_{1-4}$alkyl), and/or nitro.

3. A compound according to claim 2, or a pharmaceutically-acceptable salt, or stereoisomer, thereof, wherein, R$_2$ is selected from C$_{1-4}$alkyl, NR$_7$R$_8$, and C$_{1-4}$alkyl substituted with a group NR$_7$R$_8$;

R$_7$ and R$_8$ are independently selected from hydrogen, C$_{1-6}$alkyl, and C$_{3-6}$cycloalkyl, wherein each of said groups R$_7$ and R$_8$ are in turn optionally substituted with one to two of OH, O(C$_{1-4}$alkyl), imidazolyl, pyridyl, phenyl, tetrahydrofuryl, NH$_2$, NH(C$_{1-4}$alkyl), N(C$_{1-4}$alkyl)$_2$, and N-morpholinyl, or alternatively, R$_7$ and R$_8$ are taken together with the nitrogen atom to which they are attached to form a morpholinyl, piperidinyl, or piperazinyl ring.

4. A compound according to claim 1, or a pharmaceutically-acceptable salt, or stereoisomer, thereof, wherein ring Q is a group

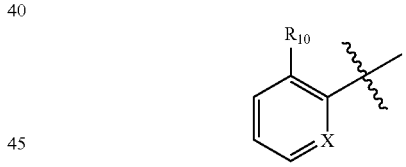

wherein R$_{10}$ is halogen, cyano, or trifluoromethyl, and X is CH.

5. A compound according to claim 4, or a pharmaceutically-acceptable salt, or stereoisomer, thereof, wherein R$_2$ is NH$_2$ or CH$_3$.

6. A compound according to claim 1, having the formula,

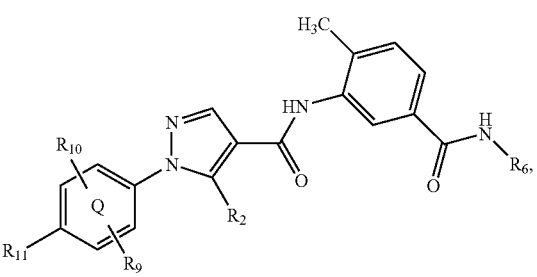

or a pharmaceutically-acceptable salt, or stereoisomer, thereof, wherein $R_6$ is $C_{1-4}$alkyl or cyclopropyl; Q is a phenyl, pyridazinyl, pyrimidinyl, or pyrazinyl ring, and $R_9$, $R_{10}$, and $R_{11}$ are each independently selected from hydrogen, $C_{1-4}$alkyl, $O(C_{1-4}alkyl)$, halogen, halo$C_{1-4}$alkyl, cyano, $SO_2(C_{1-4}alkyl)$.

7. A compound according to claim 6, or a pharmaceutically-acceptable salt, solvate, hydrate or stereoisomer, thereof, wherein $R_6$ is cyclopropyl.

8. A compound according to claim 6, or a pharmaceutically-acceptable salt, or stereoisomer, thereof, wherein $R_2$ is $C_{1-4}$alkyl or $NR_7R_8$, wherein $R_7$ is hydrogen or $C_{1-4}$alkyl, and $R_8$ is hydrogen, $C_{1-4}$alkyl, $C_{3-6}$cycloalkyl, or a $C_{1-4}$alkyl substituted with OH, methoxy, pyridyl, tetrahydrofuryl, $NH_2$, $NHC_{1-4}alkyl$, $N(C_{1-4}alkyl)_2$, imidazolyl, and N-morpholinyl; or alternatively, $R_7$ and $R_8$ combine to form morpholinyl, piperidinyl, or piperazinyl.

9. A compound according to claim 8, or a pharmaceutically-acceptable salt, or stereoisomer, thereof, wherein ring Q is a group

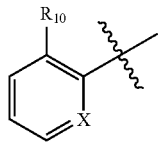

wherein $R_{10}$ is halogen, cyano, or trifluoromethyl, and X is CH.

10. A compound having the formula,

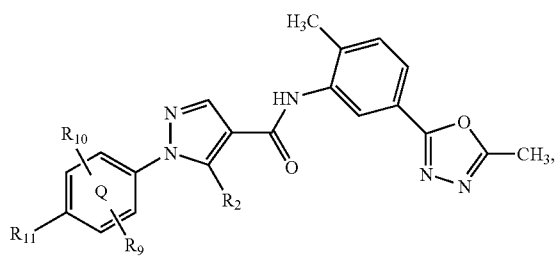

or a pharmaceutically-acceptable salt, or stereoisomer, thereof, wherein

Q is a phenyl, pyridazinyl, pyrimidinyl, or pyrazinyl ring;

$R_2$ is selected from $C_{1-6}$alkyl, amino, alkylamino, substituted alkylamino, cycloamino, substituted cycloamino, and $C_{1-6}$alkyl substituted with one to two of amino, alkylamino, substituted alkylamino, cycloamino, and/or substituted cycloamino; and $R_9$, $R_{10}$, and $R_{11}$ are each independently selected from hydrogen, $C_{1-4}$alkyl, $O(C_{1-4}alkyl)$, halogen, halo$C_{1-4}$alkyl, cyano, $SO_2(C_{1-4}alkyl)$, and nitro.

11. A compound according to claim 10, or a pharmaceutically-acceptable salt, or stereoisomer, thereof, wherein $R_2$ is $C_{1-4}$alkyl or $NR_7R_8$, wherein $R_7$ is hydrogen or $C_{1-4}$alkyl, and $R_8$ is hydrogen, $C_{1-4}$alkyl, $C_{3-6}$cycloalkyl, or a $C_{1-4}$alkyl substituted with OH, methoxy, pyridyl, tetrahydrofuryl, $NH_2$, $NHC_{1-4}alkyl$, $N(C_{1-4}alkyl)_2$, imidazolyl or N-morpholinyl; or alternatively, $R_7$ and $R_8$ combine to form morpholinyl, piperidinyl, or piperazinyl.

12. A compound according to claim 10, or a pharmaceutically-acceptable salt, or stereoisomer, thereof, wherein ring Q is a group

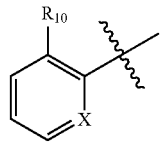

wherein $R_{10}$ is halogen, cyano, or trifluoromethyl, and X is CH.

13. A pharmaceutical composition comprising at least one compound according to claim 1 and a pharmaceutically-acceptable carrier or diluent.

14. A pharmaceutical composition comprising at least one compound according to claim 10 and a pharmaceutically-acceptable carrier or diluent.

* * * * *